US009188566B2

(12) United States Patent
Georgeson et al.

(10) Patent No.: US 9,188,566 B2
(45) Date of Patent: Nov. 17, 2015

(54) ULTRASOUND INSPECTION SYSTEM OF LIMITED ACCESS COMPOSITE STRUCTURES

(75) Inventors: Gary E. Georgeson, Tacoma, WA (US); Richard H. Bossi, Renton, WA (US); Clarence L. Gordon, III, Renton, WA (US); Jeffrey R. Kollgaard, Seattle, WA (US); William P. Motzer, Seattle, WA (US); Alan Frank Stewart, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 312 days.

(21) Appl. No.: 13/526,698

(22) Filed: Jun. 19, 2012

(65) Prior Publication Data

US 2013/0333472 A1   Dec. 19, 2013

(51) Int. Cl.
  *G01N 29/24* (2006.01)

(52) U.S. Cl.
  CPC .... *G01N 29/2418* (2013.01); *G01N 2291/0231* (2013.01); *G01N 2291/2694* (2013.01)

(58) Field of Classification Search
  CPC ... G01N 29/12; G01N 29/2418; G01N 29/46; G01N 2291/014; G01N 2291/02854; G01N 2291/2623; G01N 2291/0422; G01N 2291/0423; G01N 2291/106; G01N 2291/0421; G01N 29/24; G01N 29/04; G01N 29/265; G01N 2291/0231; G01N 2291/2694; G01N 21/17; G01N 21/1702; G01N 2021/1706; G01N 2021/1702
  USPC .......... 73/643, 655, 657, 584, 621, 633, 634, 73/245, 253; 356/237.1, 502
  See application file for complete search history.

(56) References Cited

U.S. PATENT DOCUMENTS

| 4,295,738 | A  | * | 10/1981 | Meltz et al. ..................... 356/32 |
| 4,567,769 | A  | * | 2/1986  | Barkhoudarian ............... 73/643 |
| 5,760,904 | A  |   | 6/1998  | Lorraine et al. |
| 6,144,685 | A  |   | 11/2000 | Iwasa et al. |
| 6,901,157 | B2 |   | 5/2005  | Ogawa |
| 7,042,563 | B2 | * | 5/2006  | Wilsher et al. ............. 356/237.1 |
| 7,369,250 | B2 |   | 5/2008  | Dubois et al. |
| 7,576,848 | B2 | * | 8/2009  | Dubois et al. ............... 356/237.1 |
| 7,784,348 | B2 | * | 8/2010  | Dubois et al. ................... 73/643 |
| 7,791,739 | B2 |   | 9/2010  | Dubois et al. |
| 7,800,762 | B2 |   | 9/2010  | Deaton, Jr. et al. |
| 7,865,316 | B2 |   | 1/2011  | Turner et al. |

(Continued)

OTHER PUBLICATIONS

Fomitchov et al., "Laser Ultrasonic Array System for Real-Time Cure Monitoring of Polymer-Matrix Composites," Journal of Composite Materials, vol. 36, No. 15, Aug. 2002, pp. 1889-1901.

(Continued)

*Primary Examiner* — Laura Martin
*Assistant Examiner* — Rose M Miller
(74) *Attorney, Agent, or Firm* — Yee & Associates, P.C.

(57) ABSTRACT

A method for and apparatus for inspecting a location on a test object with a number of obstructions to reaching the location. An elongate optical fiber carrier holding a number of optical fibers is moved to the location on the test object with the number of obstructions to reaching the location. A pattern of light is transmitted from the number of optical fibers onto a surface of the test object at the location. The pattern of the light is configured to cause sound waves in the test object when the pattern of the light encounters the surface of the test object. A response is detected to the sound waves using the number of optical fibers.

14 Claims, 18 Drawing Sheets

(56) References Cited

U.S. PATENT DOCUMENTS

| | | | |
|---|---|---|---|
| 8,109,160 | B2 | 2/2012 | Bossi et al. |
| 8,224,485 | B2* | 7/2012 | Unsworth ............ 700/245 |
| 8,312,773 | B2* | 11/2012 | Fomitchov ............ 73/643 |
| 2004/0003662 | A1 | 1/2004 | Kenderian et al. |
| 2008/0291963 | A1 | 11/2008 | Deaton, Jr. et al. |
| 2010/0139405 | A1 | 6/2010 | Melikechi et al. |
| 2010/0154549 | A1 | 6/2010 | Fomitchov |
| 2010/0291599 | A1 | 11/2010 | Tague, Jr. et al. |
| 2012/0304774 | A1 | 12/2012 | Ishioka |

OTHER PUBLICATIONS

Wang et al., "Beam shaping technology for laser diode arrays," Proceedings of SPIE, vol. 4770, Jul. 2002, pp. 131-135.

Bossi et al., "Laser Ultrasound Array Systems," U.S. Appl. No. 13/527,021, filed Jun. 19, 2012 (62 Pages).

Bossi et al., "Ultrasound Inspection System for Inspecting a Test Object with Non-Planar Features," U.S. Appl. No. 13/526,853, filed Jun. 19, 2012 (62 Pages).

Bossi et al., "Ultrasound Inspection System for Inspecting a Test Object with Non-Planar Features," U.S. Appl. No. 13/596,977, filed Aug. 28, 2012, 107 pages.

Intellectual Property Office of Singapore Search Report and Written Opinion, dated Jul. 3, 2014, regarding Application No. 201304652-9, 12 pages.

Office Action, dated Jun. 6, 2014, regarding U.S. Appl. No. 13/526,853, 33 pages.

Office Action, dated Jun. 26, 2014, regarding U.S. Appl. No. 13/527,021, 28 pages.

Final Office Action, datedOct. 22, 2014, regarding U.S. Appl. No. 13/526,853, 28 pages.

Final Office Action, dated Oct. 28, 2014, regarding U.S. Appl. No. 13/527,021, 33 pages.

Office Action, dated Aug. 14, 2014, regarding U.S. Appl. No. 13/596,944, 40 pages.

Office Action, dated Jan. 5, 2015, regarding U.S. Appl. No. 13/527,021, 25 pages.

Office Action, dated Feb. 18, 2015, regarding U.S. Appl. No. 13/596,944, 31 pages.

Office Action, dated Apr. 15, 2015, regarding U.S. Appl. No. 13/526,853, 16 pages.

Office Action, dated Apr. 15, 2015, regarding U.S. Appl. No. 13/527,021, 17 pages.

Notice of Allowance, dated Jun. 5, 2015, regarding U.S. Appl. No. 13/527,021, 11 pages.

* cited by examiner

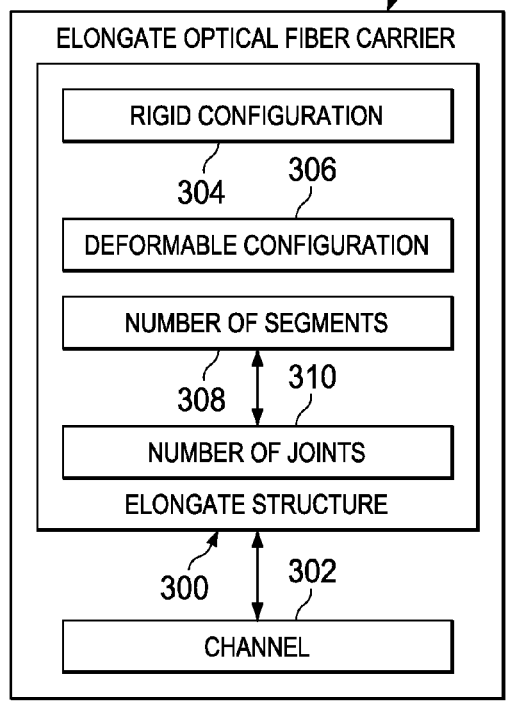
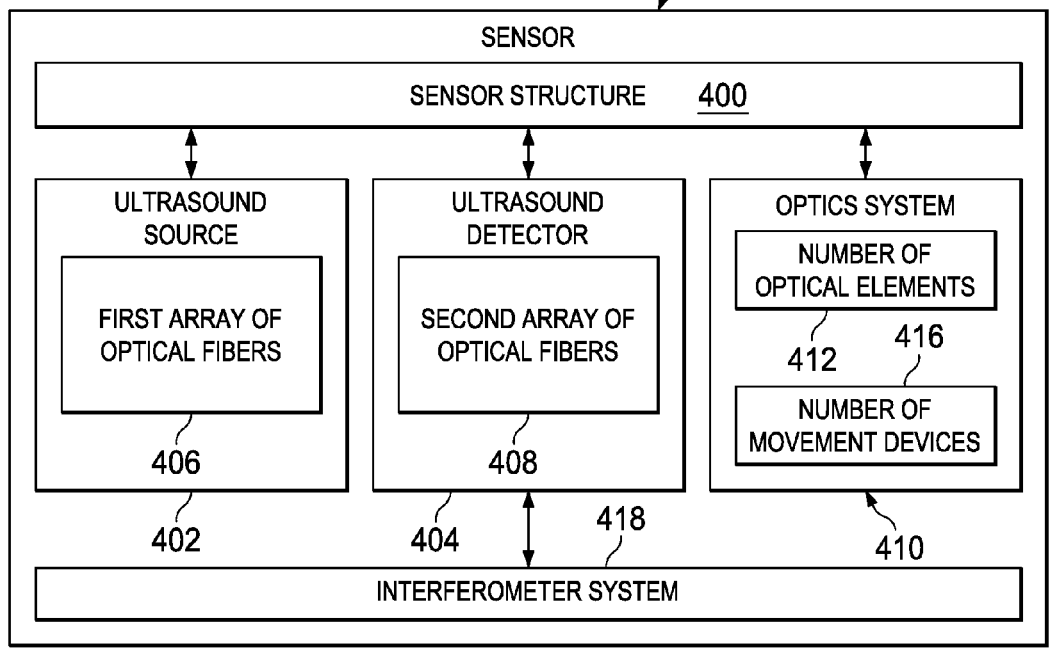

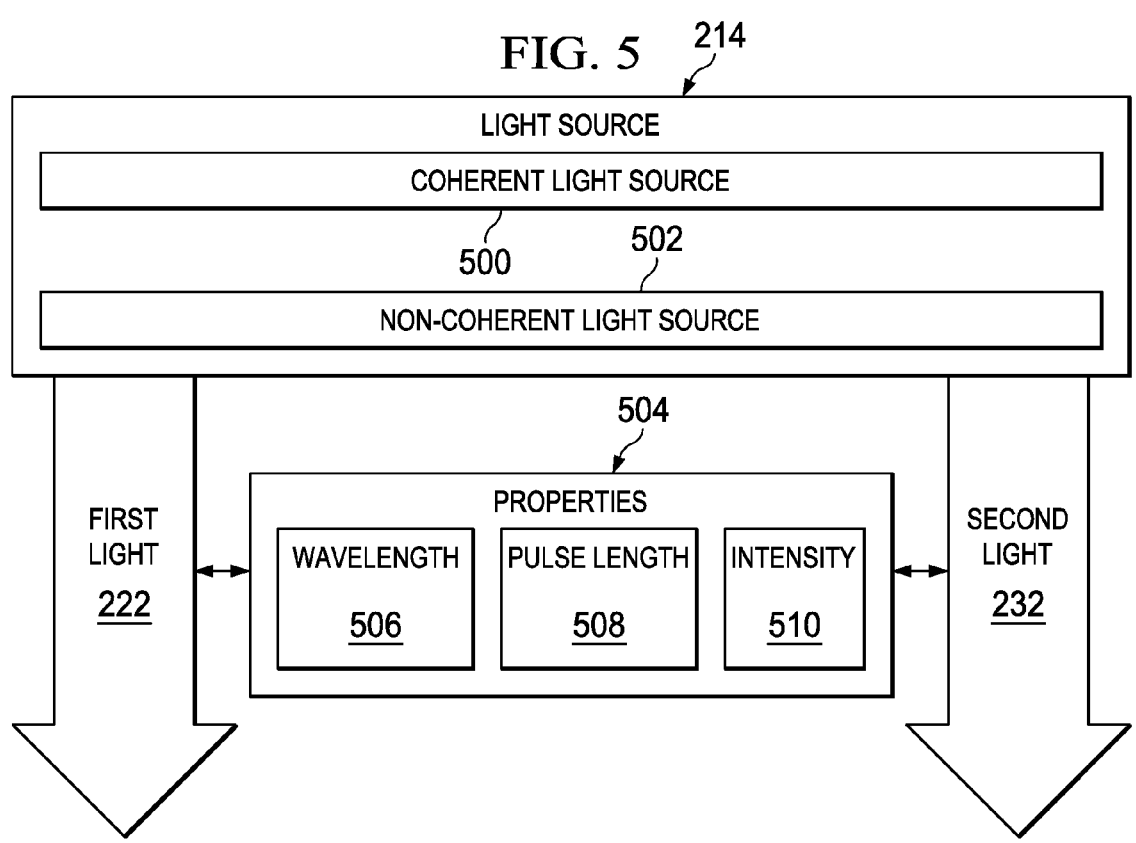

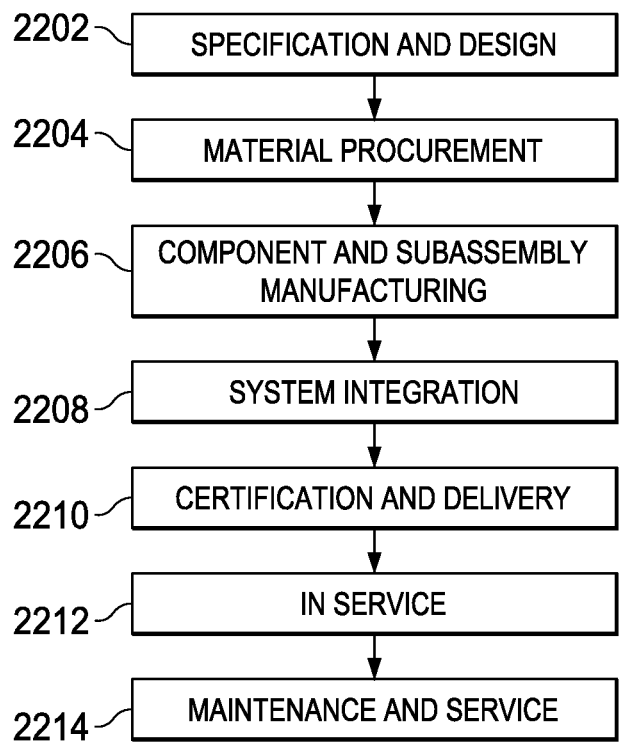
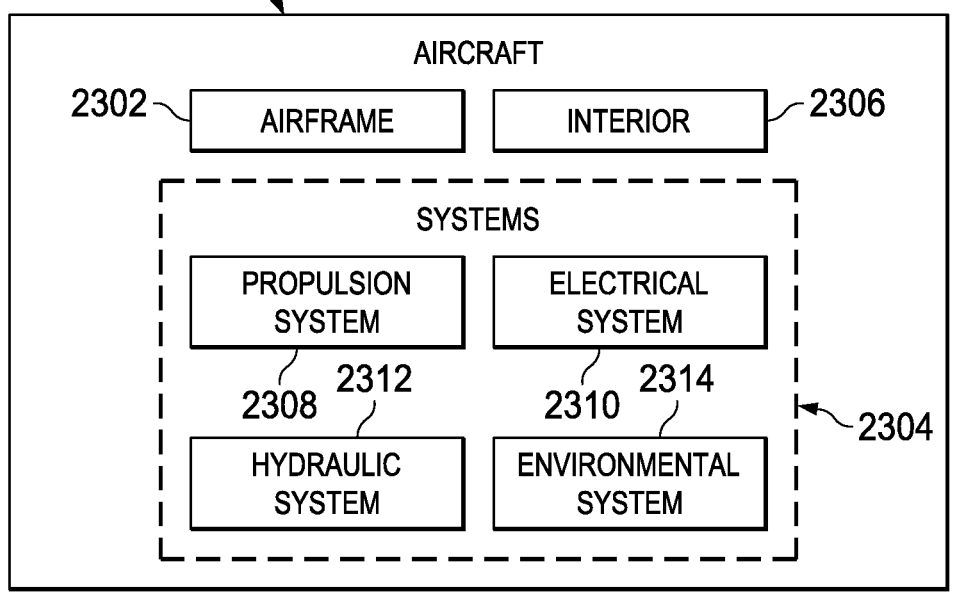

ULTRASOUND INSPECTION SYSTEM OF LIMITED ACCESS COMPOSITE STRUCTURES

CROSS-REFERENCE TO RELATED APPLICATION

This application is related to the following patent application Ser. No. 13/527,021, entitled "Laser Ultrasound Array System," and Ser. No. 13/526,653, entitled "Ultrasound Inspection System for Inspecting a Test Object with Non-Planar Features," filed of even date herewith, assigned to the same assignee, and incorporated herein by reference.

BACKGROUND INFORMATION

1. Field

The present disclosure relates generally to inspecting objects and, in particular, to performing nondestructive inspection of objects using ultrasound inspection. Still more particularly, the present disclosure relates to a method and apparatus for inspecting composite objects with limited access using ultrasound inspection.

2. Background

In manufacturing aircraft, vehicles, and other structures, inspection of parts used to form these structures is often performed to determine whether the parts will have desired parameters for a desired performance of the part. Additionally, the structures and parts are inspected as part of normal maintenance when the aircraft, vehicles, and other structures are in use.

Nondestructive testing is commonly performed on these parts. Nondestructive testing is used to evaluate the properties of a part without altering the ability to use the part in service.

Ultrasound testing is a type of nondestructive testing. Ultrasound testing is often used to perform inspections on aircraft parts that include or are comprised of composite materials. Ultrasound testing involves transmitting sound waves through a test object, such as an aircraft part or structure.

Ultrasound testing is commonly performed using a transducer. The transducer is configured to send sound waves into a test object and detect a response to the sound waves. The response to these sound waves is analyzed to determine whether inconsistencies are present in the test object.

The transducer is typically coupled to a surface of the test object. This coupling involves physical contact between the transducer and the test object. In most cases, a coupling medium is also employed. For example, water, oil, a water-based gel, or some other liquid may be used. A semi-solid material like rubber can also be used as a coupling medium. This coupling medium is often used to reduce the acoustic impedance between the transducer and the test object.

In some cases, coupling the transducer to the surface of the test object may be more difficult to perform than desired. These test objects may have various shapes and configurations. These shapes and configurations may make inspection more difficult. For example, curved shapes, corners, fittings, or other non-planar structures may be more difficult to inspect than desired.

Further, some locations within an aircraft may be more difficult to inspect than desired. For example, enclosed spaces within the aircraft are particularly difficult to inspect because other structures may obscure the path of the ultrasound inspection system. These obscured locations may have mechanical and/or electrical structures obscuring the path of the inspection system to the surface of the object under test.

Additionally, some enclosed spaces within an aircraft may limit the type of inspection that may be used to inspect the structures within the enclosed spaces. For example, an enclosed space may be smaller than the transducer array for the ultrasound inspection system.

One example of an enclosed space may be a cavity in a structure such as a fuel tank. Access to the cavity may be through an opening that may not allow access by currently used ultrasound inspection systems.

Moreover, some currently used inspection systems for small spaces are not as accurate as desired. For example, the design of currently used ultrasound inspection systems may not be able to inspect as much of the structure within the space as desired by the operator. For example, when inspecting fuel tanks, wing boxes, electrical boxes, ventilation systems, or other structures, some currently used inspection systems may not be capable of inspecting as much of these structures as desired.

Further, when a selected structure to be inspected in an aircraft is obstructed by other structures, disassembly of one or more of the structures blocking the selected structure may be needed to perform inspection of the selected structure. During routine maintenance, disassembly of a structure may take more time or manpower than desired. As a result, disassembly of the structure to inspect all surfaces of the structure may be more expensive than desired.

For example, when ultrasound testing is used to inspect the internal surfaces of a wing of an aircraft, the wing may need to be disassembled. This disassembly of the wing may put the aircraft out of service for longer than desired.

As a result, these surfaces may not be inspected as often as desired. In some cases, disassembly of some or all of the wing may be infeasible. Thus, inspections require using other techniques other than ultrasound inspection systems. These systems may be more expensive or may not provide a desired level of inspection.

Therefore, it would be desirable to have a method and apparatus that takes into account at least some of the issues discussed above, as well as other possible issues.

SUMMARY

In one illustrative embodiment, a method for inspecting a location on a test object with a number of obstructions to reaching the location is present. An elongate optical fiber carrier holding a number of optical fibers is moved to the location on the test object with the number of obstructions to reaching the location. A pattern of light is transmitted from the number of optical fibers onto a surface of the test object at the location. The pattern of the light is configured to cause sound waves in the test object when the pattern of the light encounters the surface of the test object. A response is detected to the sound waves using the number of optical fibers.

In another illustrative embodiment, an apparatus comprises a number of optical fibers and an elongate optical fiber carrier. The number of optical fibers is configured to transmit a pattern of light onto a test object. The pattern of the light is configured to cause sound waves in a test object. The elongate optical fiber carrier is configured to hold the number of optical fibers and move to a location on the test object with a number of obstructions to reaching the location.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 3 is an illustration of a block diagram of an elongate structure in accordance with an illustrative embodiment;

FIG. 4 is an illustration of a block diagram of a sensor in accordance with an illustrative embodiment;

FIG. 5 is an illustration of a block diagram of a light source in accordance with an illustrative embodiment;

FIG. 22 is an illustration of an aircraft manufacturing and service method in accordance with an illustrative embodiment; and FIG. 23 is an illustration of an aircraft in which an illustrative embodiment may be implemented.

DETAILED DESCRIPTION

The illustrative embodiments recognize and take into account one or more different considerations. For example, the different illustrative embodiments recognize and take into account that currently used ultrasound inspection systems may be unable to inspect test objects in which one or more obstructions are present.

The illustrative embodiments recognize and take into account that an ultrasound testing system may be used to reach locations with obstructions. One or more illustrative embodiments provide a method and apparatus for inspecting a location on a test object in which a number of obstructions to reaching the desired location are present. A number of optical fibers is moved to the location on the test object in which the number of obstructions to reaching the location are present. A pattern of light is transmitted from the optical fibers onto a surface of the test object at the location. The light is configured to cause sound waves in the test object when the pattern of light encounters the surface of the test object. A response to the sound waves is detected using the number of optical fibers. These optical fibers may be connected to or be a part of sensor systems, such as a system of one or more interferometers.

Figure 1:
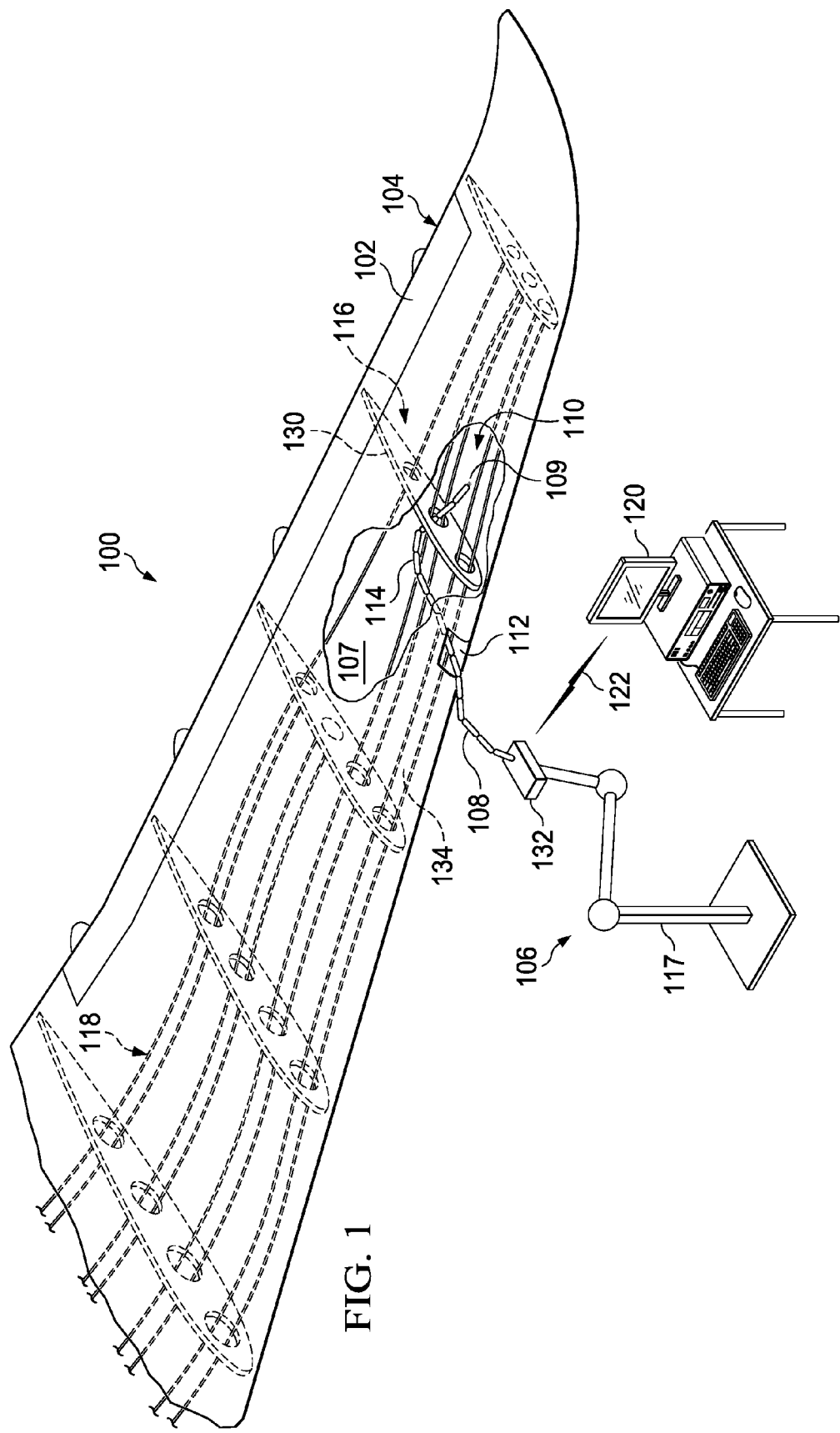
FIG. 1 is an illustration of an inspection environment in accordance with an illustrative embodiment.

With reference now to the figures and, in particular, with reference to FIG. 1, an illustration of an inspection environment is depicted in accordance with an illustrative embodiment. As depicted, inspection environment 100 includes test object 102. In this illustrative example, test object 102 takes the form of a composite test object. Test object 102 takes the form of composite wing 104.

Ultrasound inspection system 106 may be used to inspect test object 102. In particular, ultrasound inspection system 106 may be used to inspect interior 107 of composite wing 104. As depicted, ultrasound inspection system 106 includes elongate optical fiber carrier 108, number of optical fibers 109, interferometer system 132, platform 117, and computer 120.

Elongate optical fiber carrier 108 is configured to hold number of optical fibers 109. Elongate optical fiber carrier 108 is configured to be moved to inspect location 110 in interior 107 of composite wing 104.

In these illustrative examples, elongate optical fiber carrier 108 may be configured to move through or around obstructions in composite wing 104. As depicted, the obstructions may be different sizes of spaces 134 in composite wing 104 as well as different structures located within composite wing 104.

As depicted, opening 112 is an example of a small space that forms an obstruction to inspecting interior 107 of composite wing 104. Opening 112 may be, for example, a fastener hole, an access port, or some other suitable opening. With an access port, a panel may be removed from composite wing 104 to expose the access port. Other obstructions in the way of ultrasound inspection system 106 reaching location 110 in interior 107 of composite wing 104 include lines 118 and rib 130. Lines 118 may be fuel lines, hydraulic lines, and/or other suitable types of lines in composite wing 104.

In this illustrative example, elongate optical fiber carrier 108 is configured to enter interior 107 of composite wing 104 through opening 112 in composite wing 104. The size of opening 112 may result in limited access to interior 107 of composite wing 104.

Additionally, elongate optical fiber carrier 108 is configured to move around other obstructions, such as lines 118 and rib 130 within interior 107 of composite wing 104 to reach location 110 in interior 107 of composite wing 104. One or more of these obstructions result in limited access to location 110 in interior 107 of composite wing 104.

In this illustrative example, movement system 114 is configured to move elongate optical fiber carrier 108 relative to location 110 in interior 107 of composite wing 104. As depicted, movement system 114 may be comprised of a plurality of motorized joints in elongate optical fiber carrier 108 that move segments in elongate optical fiber carrier 108 within composite wing 104. For example, movement system 114 may be configured to move elongate optical fiber carrier 108 through composite wing 104 around obstruction 116 to reach test object 102. As depicted, obstruction 116 within composite wing 104 is a rib 130.

Elongate optical fiber carrier 108 with movement system 114 may be connected to platform 117. Platform 117 may be a moveable platform in some illustrative examples. In other illustrative examples, platform 117 may be a stationary platform.

In this illustrative example, computer 120 is configured to control operation of movement system 114. Computer 120 controls movement system 114 automatically or with input received at an input device connected to computer 120 to control operation of movement system 114.

In these illustrative examples, computer 120 also is configured to receive data from the ultrasound detector in elongate optical fiber carrier 108 over communications link 122. Communications link 122 may take the form of a wireless communications link in these illustrative examples. In other illustrative examples, interferometer system 132 may generate data in the form of electrical signals that are sent over a number of wires over communications link 122. As used herein, a "number of" when used with reference to items means one or more items. For example, a number of wires is one or more wires.

Composite wing 104 may be inspected by ultrasound inspection system 106 at various times during the life of composite wing 104. For example, without limitation, composite wing 104 may be inspected during assembly of composite wing 104, routine maintenance of composite wing 104 while composite wing 104 is attached to the aircraft, reworking composite wing 104, and/or some other suitable time during the life of composite wing 104. Inspection of composite wing 104 using ultrasound inspection system 106 with elongate optical fiber carrier 108 allows structures within interior 107 of composite wing 104 to be inspected without disassembling composite wing 104. As a result, inspection of composite wing 104 using ultrasound inspection system 106 may be done more quickly and may be more cost effective than inspection using inspection systems that require disassembly of composite wing 104.

While inspection environment 100 is depicted with ultrasound inspection system 106 used to inspect composite wing 104, ultrasound inspection system 106 may be used to inspect other test objects. For example, without limitation, ultrasound inspection system 106 with elongate optical fiber carrier 108 may be used to inspect internal structures within an engine, an electrical box, an APU unit, a ventilation system, a stowage system, and/or other suitable structures. Ultrasound inspection system 106 may be used to inspect these and other structures in which obstructions are present. With ultrasound inspection system 106, the amount of time needed to inspect test objects may be reduced. Further, the amount of disassembly of the structures may be reduced or eliminated.

Figure 2:
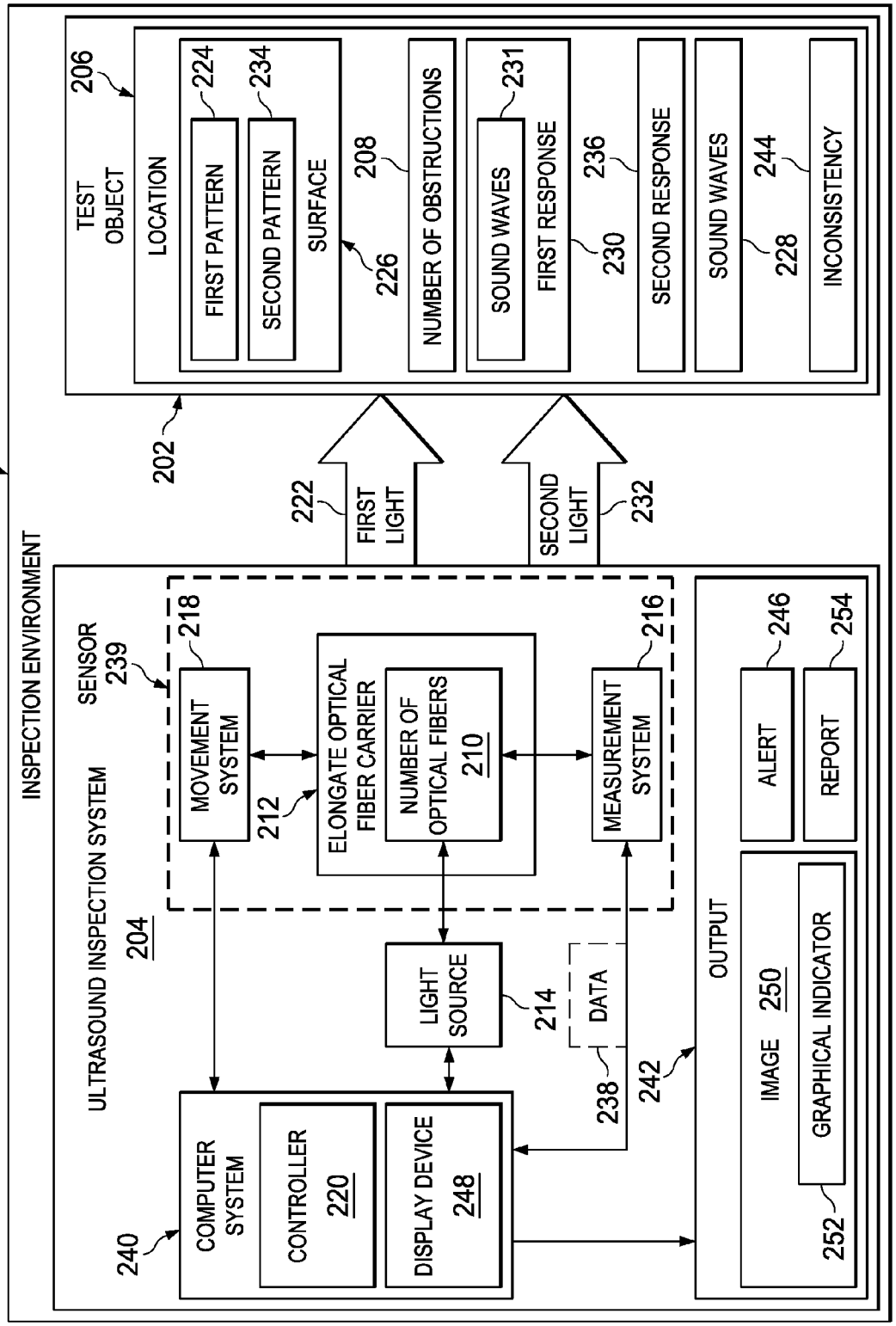
FIG. 2 is an illustration of a block diagram of an inspection environment in accordance with an illustrative embodiment.

Turning now to FIG. 2, an illustration of a block diagram of an inspection environment is depicted in accordance with an illustrative embodiment. Inspection environment 100 in FIG. 1 is one example of an implementation of inspection environment 200 shown in block form in this figure.

As illustrated, inspection environment 200 includes test object 202. Test object 202 may take any number of forms. For example, test object 202 may be a structure or part in an aircraft. In other illustrative examples, test object 202 may be comprised of multiple structures in the aircraft.

Further, test object 202 may be comprised of different types of materials. For example, without limitation, test object 202 may be comprised of a number of materials selected from at least one of a composite material, a plastic, a metal, and other suitable types of materials.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations.

In these illustrative examples, test object 202 may be a composite part for an aircraft selected from one of a panel, a fuselage barrel, a stringer, a fuel tank, a spar, a rib, a wing box, a wing, a stabilizer, and other suitable types of objects. Test object 202 may be inspected using ultrasound inspection system 204. In particular, ultrasound inspection system 204 may be used to inspect location 206 for test object 202. In this illustrative example, test object 202 may have limited access. In particular, access to location 206 in test object 202 may be limited.

In other words, number of obstructions 208 may be present with respect to accessing location 206 in test object 202. An obstruction in number of obstructions 208 may be selected from at least one of a rib, a spar, a line, a wiring bundle, a flange, an opening in a structure, a space in an interior of a structure, a channel in a structure, a cable, a pipe, a stringer, a webbing, or other structures that may reduce access to location 206 for inspection. These structures may be structures through which ultrasound inspection system 204 traverses to reach location 206.

In another illustrative example, number of obstructions 208 may be test object 202, itself. For example, test object 202 may be a cavity in test object 202 accessed by an opening. In particular, test object 202 may be a fuel tank with an opening. The opening may be smaller than feasible for currently available ultrasound systems to traverse and reach a location within the interior of the fuel tank for inspection. These openings may be, for example, without limitation, fastener holes, small access panels, a temporary hole, an opening created by an impact or other source, or other suitable openings.

In these illustrative examples, ultrasound inspection system 204 is configured to reach location 206 taking into account number of obstructions 208 to perform inspection of test object 202. In other words, ultrasound inspection system 204 is configured to bypass number of obstructions 208. For example, ultrasound inspection system 204 may pass through, move around, move between, or move in other ways to bypass number of obstructions 208.

As depicted, ultrasound inspection system 204 includes number of optical fibers 210, elongate optical fiber carrier 212, light source 214, measurement system 216, movement system 218, and controller 220.

As depicted, number of optical fibers 210 is configured to reach location 206 by moving through or around number of obstructions 208. In these illustrative examples, number of optical fibers 210 is associated with elongate optical fiber carrier 212.

When one component is "associated" with another component, the association is a physical association in these depicted examples. For example, a first component, number of optical fibers 210, may be considered to be associated with a second component, elongate optical fiber carrier 212, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

In this illustrative example, elongate optical fiber carrier 212 is configured to hold number of optical fibers 210. Further, elongate optical fiber carrier 212 is configured bypass a number of obstructions 208 to reach location 206. For example, elongate optical fiber carrier 212 may be configured to move between obstructions in number of obstructions 208 such as cables, hardware, systems, wire bundles, pipes, stringers, webbing, or other structures to reach location 206. In another example, elongate optical fiber carrier 212 may be configured to move through an obstruction in number of obstructions 208, such as an opening in test object 202, to reach location 206 within the interior of test object 202. For example, test object 202 may be a wall with an opening.

Movement system 218 is configured to move elongate optical fiber carrier 212 to location 206 in test object 202. Movement system 218 may include various types of movement devices. For example, movement system 218 may include hydraulic actuators, motors, electromechanical actuators, and other suitable types of devices.

Light source 214 is connected to number of optical fibers 210. In this illustrative example, light source 214 is configured to generate first light 222. Number of optical fibers 210 is configured to transmit first light 222 toward location 206. First light 222 is configured to cause first pattern 224 of first light 222 on surface 226 at location 206 of test object 202. In this illustrative example, first pattern 224 of first light 222 on surface 226 is configured to cause sound waves 228 in test object 202.

In this illustrative example, first pattern 224 may take various forms. For example, first pattern 224 may be a single area when number of optical fibers 210 is one optical fiber. In other illustrative examples, first pattern 224 may be areas that may or may not overlap each other. These areas may be arranged in the form of a line or some other suitable shape. The line may be contiguous or non-contiguous depending on whether the areas overlap.

First response 230 occurs as a result of sound waves 228 traveling within test object 202. First response 230 is comprised of sound waves 231. First response 230 includes sound waves 231 that may occur as a result of scattering, reflection, modulation, and other changes to sound waves 228 traveling within test object 202.

Number of optical fibers 210 is configured to detect first response 230 to sound waves 228. In these illustrative examples, first response 230 may be detected by number of optical fibers 210 transmitting second light 232 onto surface 226 of test object 202. Second light 232 has second pattern 234 when transmitted onto surface 226 of test object 202.

As depicted, second pattern 234 also may be comprised of areas of light on surface 226 in response to second light 232 transmitted by number of optical fibers 210. In these illustrative examples, second pattern 234 of second light 232 may be the same or may be different from first pattern 224 of first light 222. Number of optical fibers 210 is configured to detect second response 236. The areas of light may be contiguous or non-contiguous.

Second response 236 is second light 232 that has been deflected by first response 230 in this illustrative example. First response 230 caused by sound waves 228 traveling within test object 202 may reach surface 226 and cause changes in the index of refraction of the air at surface 226. The change in the index of refraction in the air causes light in second response 236 to travel differently.

Additionally, sound waves 231 in first response 230 may cause changes in surface 226 that result in scattering, reflection, and modulation of second light 232 transmitted as areas in second pattern 234 onto surface 226 of test object 202. The change is used to identify first response 230.

Second response 236 provides information about first response 230. Thus, second response 236 may be used to generate data 238 about first response 230.

In this illustrative example, measurement system 216 is configured to generate data 238 using second response 236. Measurement system 216 may be, for example, one or more interferometers in these illustrative examples. In these illustrative examples, number of optical fibers 210 and measurement system 216 may form sensor 239. In some illustrative examples, sensor 239 also may include elongate optical fiber carrier 212.

In this illustrative example, controller 220 is configured to receive and process data 238 from measurement system 216. Further, controller 220 is configured to control the operation of light source 214, measurement system 216, and movement system 218.

In these illustrative examples, controller 220 controls the operation of ultrasound inspection system 204. Controller 220 may be implemented using hardware, software, or a combination of the two. When software is used, the operations performed by the components may be implemented in the program code configured to be run on a processor unit. When hardware is employed, the hardware may include circuits that operate to perform the operations in the components.

In the illustrative examples, the hardware may take the form of a circuit system, an integrated circuit, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

In these illustrative examples, controller 220 may be implemented within computer system 240. Computer system 240 may be one or more computers. When more than one computer is present in computer system 240, those computers may be in communication with each other through a communications medium such as a network.

In this illustrative example, controller 220 may use data 238 to generate output 242. Output 242 may indicate whether inconsistency 244 is present in test object 202. Inconsistency 244 may be, for example, without limitation, an undesired level of porosity, delamination, and other undesired features or properties of test object 202.

Output 242 may take a number of different forms. For example, output 242 may take the form of alert 246. Alert 246 may indicate whether inconsistency 244 is present. Alert 246 may be displayed on display device 248 within computer system 240.

In another illustrative example, output 242 may be image 250. Image 250 may be displayed on display device 248. Image 250 also may be an image of a portion or all of test object 202, including graphical indicator 252 when inconsistency 244 is present in test object 202. Graphical indicator 252 may be displayed in a location in image 250 corresponding to a location in test object 202 where inconsistency 244 is detected. In other illustrative examples, if inconsistency 244 is absent, graphical indicator 252 may be displayed to indicate an absence of inconsistency 244.

As another illustrative example, output 242 may take the form of report 254. Report 254 may identify any inconsistencies for test object 202. Report 254 also may include other information such as locations of inconsistencies, types of inconsistencies, sizes of inconsistencies, and other suitable types of information. Thus, output 242 may be at least one of alert 246, image 250 with graphical indicator 252, report 254, and other suitable types of output. As a result, ultrasound inspection system 204 provides for more efficient inspection of test object 202 when number of obstructions 208 is present as compared to currently available ultrasound inspection systems.

Further, ultrasound inspection system 204 uses first light 222 and second light 232 that are transmitted through number of optical fibers 210. Elongate optical fiber carrier 212 may be configured to move to location 206 when number of obstructions 208 is present. In these illustrative examples, elongate optical fiber carrier 212 may be moved through or around number of obstructions 208 to location 206 to perform inspection of test object 202 at location 206.

In this manner, ultrasound inspection system 204 may be used to inspect test objects such as fuel tanks, wing boxes, and other structures that may have locations that are difficult to access due to number of obstructions 208 to ultrasound inspection system 204 reaching location 206 to perform an inspection of test object 202. In this manner, less disassembly and less time may be needed to inspect these and other types of test objects.

Turning now to FIG. 3, an illustration of a block diagram of an elongate structure is depicted in accordance with an illustrative embodiment. In this depicted example, examples of elongate optical fiber carrier 212 in FIG. 2 are depicted.

In this illustrative example, elongate optical fiber carrier 212 comprises elongate structure 300. Elongate structure 300 defines channel 302. Channel 302 is a channel in which number of optical fibers 210 may be held within elongate structure 300 for elongate optical fiber carrier 212.

In this illustrative example, elongate structure 300 may have, for example, rigid configuration 304 or deformable configuration 306. When elongate structure 300 has deformable configuration 306, elongate structure 300 may stay in the shape after the deformation of elongate structure 300. In other illustrative examples, elongate structure 300 may return to its original shape after being deformed.

Further, elongate structure 300 may be comprised of number of segments 308. In this illustrative example, number of segments 308 may be a single segment in which channel 302 is continuous through the segment. For example, when a single segment is present in number of segments 308, the single segment may be a sheath, a rigid sheath, a deformable sheath, a mesh, or some other suitable form.

When more than one segment is present in number of segments 308, channel 302 may be defined within the different segments and may not be continuous. When more than one segment is present in number of segments 308, those segments may be connected to each other by number of joints 310. Number of joints 310 may allow number of segments 308 to be moved to different positions and orientations. In this form, elongate structure 300 may be a segmented snake configured to change orientation and move. In other illustrative examples, the segmented snake may be configured for attachment to a robotic arm or other platform. In still other illustrative examples, elongate structure 300 may be a hand held tool with orientation control.

When more than one joint is present in number of joints 310, movement system 218 in FIG. 2 may be configured to move and position number of segments 308 relative to each other. The movement of number of segments 308 may involve moving number of segments 308 on test object 202. In other illustrative examples, movement of number of segments 308 may involve changing the position of number of segments 308 with respect to each other.

With reference now to FIG. 4, an illustration of a block diagram of a sensor is depicted in accordance with an illustrative embodiment. Examples of components in sensor 239 are shown in this figure.

As depicted, sensor 239 includes sensor structure 400, ultrasound source 402, and ultrasound detector 404. Sensor structure 400 may take a number of different forms. For example, sensor structure 400 may be a housing, a frame, or some other suitable type of physical structure. In one illustrative example, sensor structure 400 may take the form of elongate optical fiber carrier 108 in FIG. 1 and elongate optical fiber carrier 212 in FIG. 2.

In these illustrative examples, ultrasound source 402 and ultrasound detector 404 are associated with sensor structure 400. Ultrasound source 402 is configured to transmit first light 222, while ultrasound detector 404 is configured to detect sound waves 231 in first response 230 in response to sound waves 228.

Ultrasound source 402 is comprised of first array of optical fibers 406. First array of optical fibers 406 is configured to receive first light 222 from light source 214 and transmit first light 222 in the form of first pattern 224 onto surface 226 of test object 202. First light 222 from first array of optical fibers 406 is configured to cause excitation in test object 202. In other words, first light 222 from first array of optical fibers 406 is configured to generate sound waves 228 within test object 202.

As depicted, ultrasound detector 404 is comprised of second array of optical fibers 408. Second array of optical fibers 408 is configured to transmit second light 232 and detect second response 236 to second light 232. Second light 232 is not configured to generate sound waves 228 within test object 202. Instead, second light 232 is configured to reflect, scatter, or otherwise interact with surface 226 of test object 202, the air around surface 226 of test object 202, or both in a manner such that the portion of second light 232 that is received by second array of optical fibers 408 may be affected by sound waves in first response 230 that reach surface 226 of test object 202.

In some illustrative examples, if overlap is present in the time between the two patterns of light, first pattern 224 and second pattern 234 being transmitted onto surface 226. With this overlap, second array of optical fibers 408 may be used to monitor for first response 230 at the same time or prior to the generation of sound waves 228.

In other illustrative examples, each optical fiber in first array of optical fibers 406 may transmit first light 222 sequentially rather than at the same time. Additionally, groupings of optical fibers in number of optical fibers 210 may sequentially transmit first light 222. Second light 232 may be transmitted in a similar fashion by second array of optical fibers 408.

In still other illustrative examples, first light 222 may be transmitted using different phases, wavelengths, or both in addition to transmitting first light 222 through optical fibers in first array of optical fibers 406, second array of optical fibers 408, or both at different times.

Mechanisms such as delay lines and delay circuits separate lasers in light source 214. These mechanisms may reduce cross-talk in the optical fibers that results in first light 222 in first array of optical fibers 406 and second light 232 in second array of optical fibers 408 from exiting one optical fiber and entering another optical fiber. In other words, different phases, wavelengths, timings or some combination thereof may be used to reduce cross-talk between optical fibers within first array of optical fibers 406 and second array of optical fibers 408.

In these illustrative examples, sensor 239 also may include optics system 410. Optics system 410 is associated with sensor structure 400. As depicted, optics system 410 is a hardware system and may include components such as number of optical elements 412, number of movement devices 416, and other suitable components.

Optics system 410 is configured to direct the transmission of first light 222 and second light 232 to surface 226 of test object 202. Further, optics system 410 also may direct second response 236 to second array of optical fibers 408.

Number of optical elements 412 is configured to modify the transmission of first light 222 and second light 232 in these illustrative examples. Number of optical elements 412 may include at least one of a lens, a mirror, a diffractive optical element, a polarizer, a wave plate, a periodically poled Lithium niobate crystal, or other suitable optical elements.

For example, number of optical elements 412 may be configured to shape first light 222 transmitted from first array of optical fibers 406 to form first pattern 224. In a similar fashion, number of optical elements 412 may be used to shape second light 232 transmitted from second array of optical fibers 408 to form areas in second pattern 234 with a desired size. Number of optical elements 412 also may be used to change the polarization of first light 222 and second light 232, the color of first light 222 and second light 232, and other parameters of first light 222 and second light 232.

In these illustrative examples, number of movement devices 416 may be used to move one or more of number of optical elements 412 to cause movement of first pattern 224 of first light 222 and second pattern 234 of second light 232. This movement may occur without moving sensor structure 400 in this illustrative example. Number of movement devices 416 may include, for example, at least one of a motor, an actuator, and other suitable types of devices that may be configured to move number of optical elements 412.

Sensor 239 also may include interferometer system 418. Interferometer system 418 is a hardware device and is configured to identify information from the light forming second response 236. Interferometer system 418 may include one or more interferometers in these illustrative examples. The information identified by interferometer system 418 may include, for example, displacements, deflections, surface velocity, and other information that may be used to identify second response 236 as detected by second array of optical fibers 408 receiving the light in second response 236.

In some illustrative examples, interferometer system 418 may be considered part of ultrasound detector 404 even though interferometer system 418 may not be located in sensor structure 400. Interferometer system 418 may be associated with optics system 410 or may be in a separate location.

Turning now to FIG. 5, an illustration of a block diagram of a light source is depicted in accordance with an illustrative embodiment. In these illustrative examples, light source 214 in FIG. 2 may be, for example, at least one of a coherent light source 500 and non-coherent light source 502. Coherent light source 500 may be, for example, a laser, an array of laser diodes, or some other suitable source of coherent light. Non-coherent light source 502 may be, for example, an array of light emitting diodes, xenon light, or some other suitable source of non-coherent light.

As depicted, light source 214 is configured to generate, first light, first light 222, and second light, second light 232 with properties 504. Properties 504 include wavelength 506, pulse length 508, and intensity 510. Properties 504 may be different for first light 222 and second light 232.

Wavelength 506 may be selected based on the material forming test object 202, the thickness of test object 202, and other suitable factors. Wavelength 506 may be selected for first light 222 in a manner that increases absorption of energy from first light 222 when first light 222 and second light 232 are transmitted onto surface 226 of test object 202. For example, when test object 202 is comprised of one or more composite materials, wavelength 506 selected for first light 222 may be from about 300 millimeters to about 30,000 millimeters. Wavelength 506 may be the same for generating both sound waves 228 and first response 230.

Pulse length 508 may be selected for first light 222 to generate a desired frequency for sound waves 228. For example, a pulse duration of about 1 nanosecond to about 200 nanoseconds may be used. Pulse length 508 may be selected to have a duration of about 50 microseconds to about 100 microseconds for second light 232 to be used to detect sound waves 231 in first response 230.

Intensity 510 is selected based on the amount of energy that is desired to be transmitted into test object 202 by first light 222 encountering surface 226 of test object 202. Intensity 510 may be selected for first light 222 to provide a desired level of sound waves 228 when first light 222 is transmitted onto surface 226 of test object 202. Intensity 510 may be selected for first light 222 and second light 232 to reduce or avoid damage to surface 226 of test object 202. Of course, the intensity also may vary depending on the values selected for pulse length 508.

Although specific values have been specified for properties 504, these values are only presented for purposes of illustration and not meant to limit other values that may be used. The selection of properties 504 may vary depending on light source 214, materials in test object 202, and other factors.

The illustration of inspection environment 200 and the different components in inspection environment 200 in FIGS. 2-5 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative embodiments, ultrasound source 402 and ultrasound detector 404 may be placed in separate sensor structures. In other illustrative examples, sensor 239 may be moved by a human operator rather than a robot or other type of machine. In other words, movement system 218 may take the form of a human operator.

In still another illustrative example, optics system 410 may be implemented using more than one block. For example, optics system 410 may be part of ultrasound source 402, ultrasound detector 404, or both rather than being a separate block.

In another illustrative example, test object 202 may be an object for other types of platforms other than an aircraft. The platform in which the test object may be located may be, for example, a mobile platform, a stationary platform, a land-based structure, an aquatic-based structure, and a space-based structure. More specifically, the platform may be a surface ship, a tank, a personnel carrier, a train, a spacecraft, a space station, a satellite, a submarine, an automobile, a power plant, a bridge, a claim, a manufacturing facility, a building, and other suitable platforms.

In another illustrative example, movement system 218 is shown as a separate block from elongate optical fiber carrier 212. These components, however, may be combined in some illustrative examples. In other words, movement system 218 may be part of elongate optical fiber carrier 212 in some illustrative examples.

In another illustrative example, a portion of light source 214 may be implemented as part of measurement system 216. For example, when measurement system 216 takes the form of an interferometer, measurement system 216 may also generate second light 232 in addition to detecting second response 236.

In still another illustrative example, number of optical fibers 210 and sensor 239 may be distributed in two or more elongate optical fiber carriers. For example, a first portion of number of optical fibers 210 may be held in elongate optical fiber carrier 212 and a second portion of optical fibers 210 may be held in a second optical fiber carrier. In this example, the first portion of number of optical fibers 210 may transmit first light 222. The second portion of number of optical fibers 210 may transmit second light 232 and detect second response 236.

Figure 6:
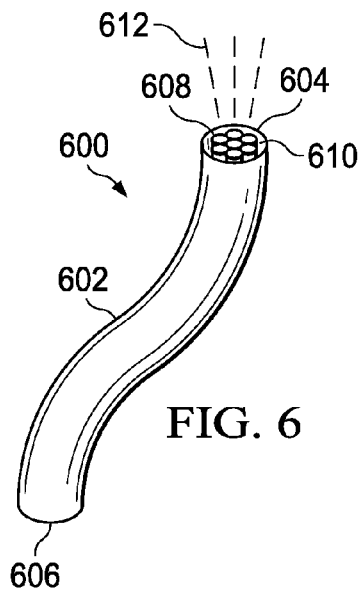
FIG. 6 is an illustration of an elongate optical fiber carrier in accordance with an illustrative embodiment.

Turning now to FIG. 6, an illustration of an elongate optical fiber carrier is depicted in accordance with an illustrative embodiment. In this depicted example, elongate optical fiber carrier 600 is an example of one implementation of elongate optical fiber carrier 212 shown in block form in FIG. 2.

In this depicted example, elongate optical fiber carrier 600 includes elongate structure 602, which has first end 604 and second end 606. Elongate structure 602 for elongate optical fiber carrier 600 is configured to carry number of optical fibers 608 within channel 610 of elongate structure 602. In this illustrative example, elongate structure 602 is deformable and may be bent to different orientations.

As depicted, light 612 may be emitted from number of optical fibers 608 at first end 604. Second end 606 may be connected to a movement system such as movement system 218 in FIG. 2.

Figure 7:
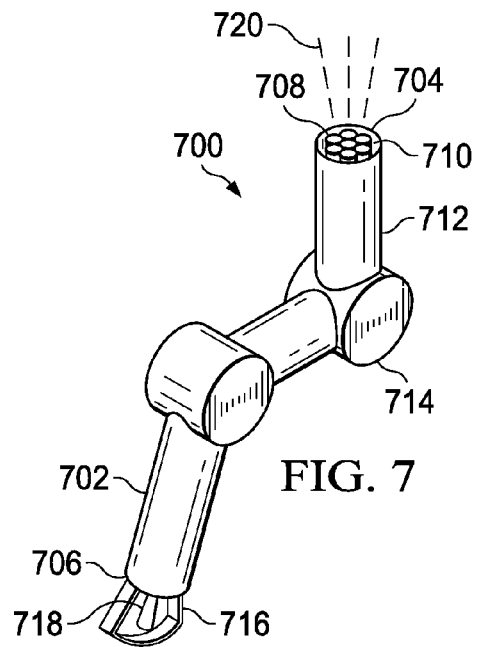
FIG. 7 is an illustration of an elongate optical fiber carrier in accordance with an illustrative embodiment.

With reference now to FIG. 7, an illustration of an elongate optical fiber carrier is depicted in accordance with an illustrative embodiment. In this depicted example, elongate optical fiber carrier 700 is an example of an implementation for elongate optical fiber carrier 212 shown in block form in FIG. 2.

In this illustrative example, elongate optical fiber carrier 700 has elongate structure 702. Elongate structure 702 has first end 704 and second end 706. As depicted, number of optical fibers 708 within channel 710 may be carried by elongate structure 702.

As depicted, elongate structure 702 is comprised of segments 712. Segments 712 are connected to each other through joints 714. In this illustrative example, segments 712 are rigid segments. Segments 712 may be positioned relative to each other at joints 714. Changing the position of segments 712 relative to each other may change the shape of channel 710 and the number of optical fibers 708.

In this illustrative example, elongate optical fiber carrier 700 includes handle 716 at second end 706 of elongate structure 702. Handle 716 is configured to be held by a human operator. Additionally, handle 716 also may include control 718 that may be manipulated to change the position of segments 712 relative to each other. For example, movement of segments 712 may be controlled by cables running around pulleys at each joint in joints 714. The cables may be attached to handle 716. In another example, each joint in joints 714 may be controlled by geared stepper motors in joints 714. In this illustrative example, light 720 may be emitted from number of optical fibers 708 at first end 704 of elongate optical fiber carrier 700.

Figure 8:
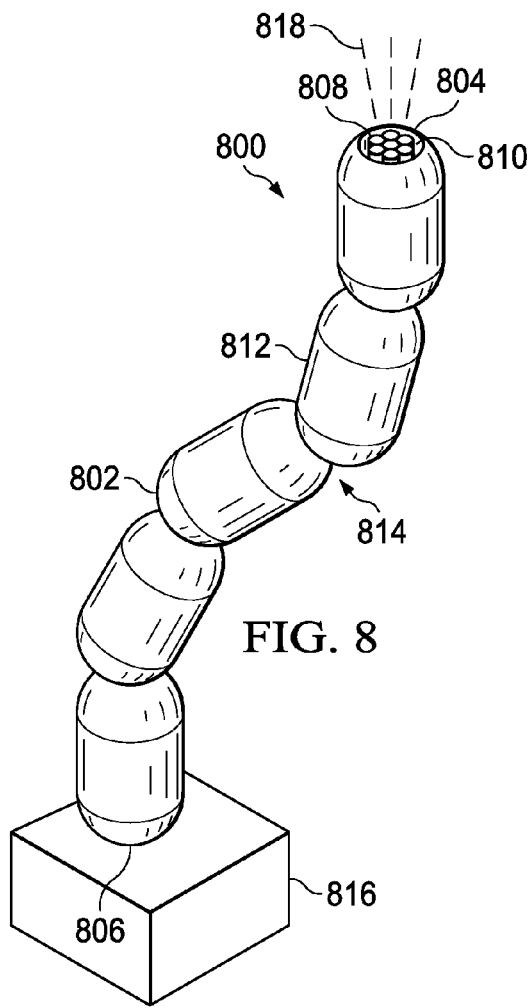
FIG. 8 is an illustration of an elongate optical fiber carrier in accordance with an illustrative embodiment.

Turning now to FIG. 8, an illustration of an elongate optical fiber carrier is depicted in accordance with an illustrative embodiment. In this depicted example, elongate optical fiber carrier 800 is an example of an implementation for elongate optical fiber carrier 212 shown in block form in FIG. 2.

In this illustrative example, elongate optical fiber carrier 800 has elongate structure 802. Elongate structure 802 has first end 804 and second end 806. Number of optical fibers 808 may be located within channel 810 of elongate structure 802.

As depicted, elongate structure 802 is comprised of segments 812. These segments are connected to each other by joints 814. Joints 814 allow positioning of segments 812 relative to each other.

Second end 806 of elongate structure 802 is connected to pedestal robot 816. Pedestal robot 816 may move elongate optical fiber carrier 800 to different locations relative to a test object. In this illustrative example, light 818 may be emitted by number of optical fibers 808 at first end 804 of elongate structure 802.

Figure 9:
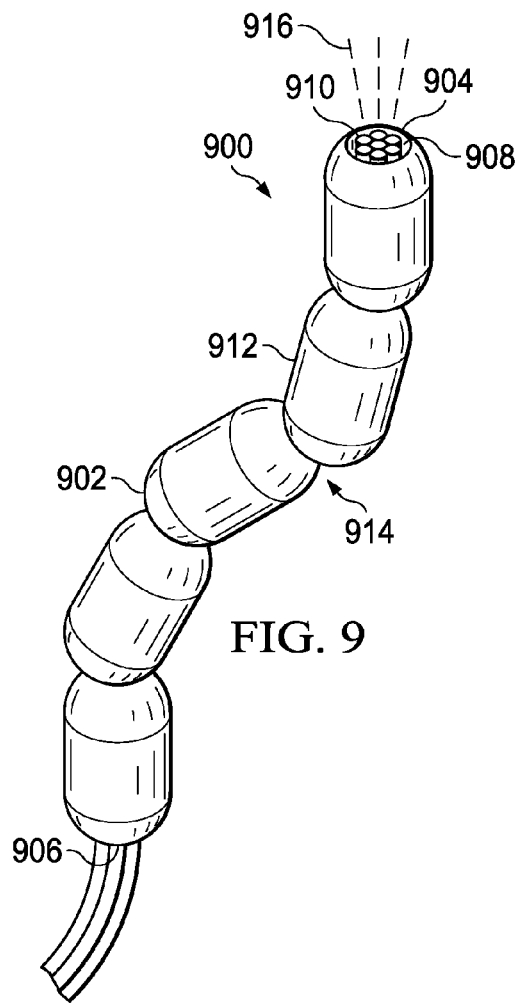
FIG. 9 is an illustration of an elongate optical fiber carrier in accordance with an illustrative embodiment.

Turning now to FIG. 9, an illustration of an elongate optical fiber carrier is depicted in accordance with an illustrative embodiment. In this depicted example, elongate optical fiber carrier 900 is an example of an implementation of elongate optical fiber carrier 212 shown in block form in FIG. 2.

In this illustrative example, elongate optical fiber carrier 900 includes elongate structure 902. Elongate structure 902 has first end 904 and second end 906. Elongate structure 902 has channel 908 which holds number of optical fibers 910.

Elongate structure 902 is comprised of segments 912 that are joined to each other by joints 914. In this illustrative example, segments 912 may move relative to each other to change positions. Additionally, segments 912 also may be motorized such that elongate optical fiber carrier 900 may move on a test object or other structure without requiring a human operator or a robot. In these illustrative examples, light 916 may be transmitted by number of optical fibers 910 at first end 904 of elongate structure 902.

Figure 10:
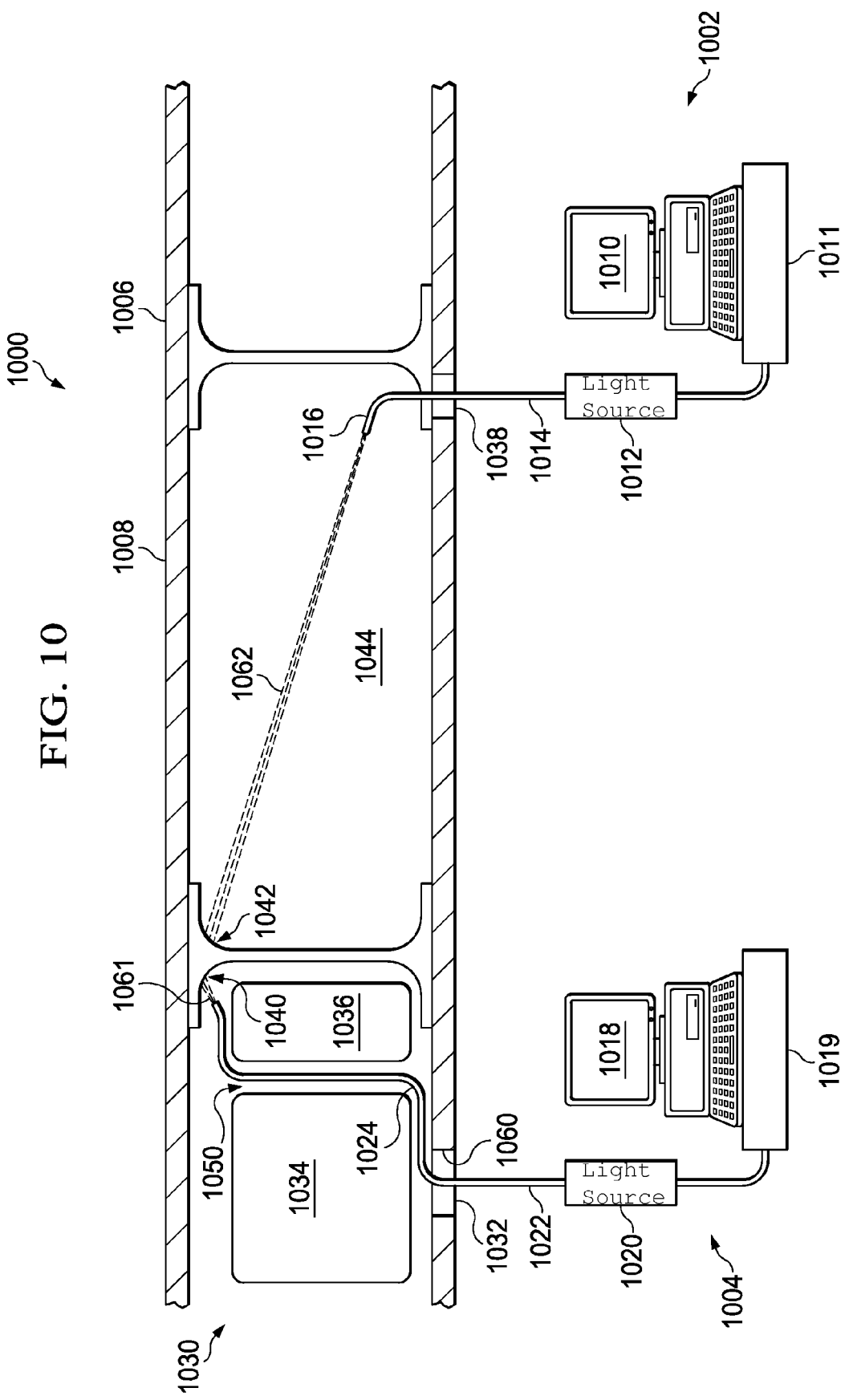
FIG. 10 is an illustration of an inspection environment in accordance with an illustrative embodiment.

Turning now to FIG. 10, an illustration of an inspection environment is depicted in accordance with an illustrative embodiment. In this depicted example, inspection environment 1000 is an example of an implementation for inspection environment 200 in FIG. 2.

As depicted, ultrasound inspection system 1002 and ultrasound inspection system 1004 may be used to inspect test object 1006. In this illustrative example, test object 1006 takes the form of wing box 1008.

Ultrasound inspection system 1002 includes computer 1010, measurement system 1011, light source 1012, number of optical fibers 1014, and elongate optical fiber carrier 1016. Ultrasound inspection system 1004 comprises computer 1018, measurement system 1019, light source 1020, number of optical fibers 1022, and elongate optical fiber carrier 1024. In this illustrative example, obstructions 1030 are present with respect to testing locations in test object 1006. In this illustrative example, obstructions 1030 include obstruction 1032, obstruction 1034, obstruction 1036, and obstruction 1038.

Obstructions 1030 reduce accessibility to locations such as location 1040 and location 1042 in interior 1044 of test object 1006 in these illustrative examples. For example, space available for access to interior 1044 of test object 1006 may be limited by obstructions 1030. Obstruction 1032 is an example of one of obstructions 1030 in interior 1044. Obstruction 1032 is an access port.

In this illustrative example, obstruction 1034 and obstruction 1036 may be spars, ribs, or other structures within test object 1006. As can be seen, obstruction 1034 and obstruction 1036 form restricted space 1050 within interior 1044 of test object 1006.

As can be seen, elongate optical fiber carrier 1024 may be moved through access port 1060 and restricted space 1050 to reach location 1040 within interior 1044 of test object 1006. In this illustrative example, elongate optical fiber carrier 1024 may be changed in configuration to reach location 1040. When positioned within interior 1044, light 1061 may be emitted from number of optical fibers 1022 toward location 1040.

Ultrasound inspection system 1002 is configured to inspect location 1042 in interior 1044 of test object 1006. In this illustrative example, elongate optical fiber carrier 1016 may be moved through obstruction 1038 which takes the form of a fastener hole in this illustrative example.

Elongate optical fiber carrier 1016 may be moved into interior 1044 through obstruction 1038 to perform inspection of location 1042 within interior 1044 of test object 1006. When in a desired position, light 1062 may be emitted from number of optical fibers 1014 toward location 1042.

In this manner, ultrasound inspection system 1002 and ultrasound inspection system 1004 may be operated to inspect test object 1006. In particular, the inspection may be made for locations such as location 1040 and location 1042 in interior 1044 of test object 1006. As depicted, elongate optical fiber carrier 1016 and elongate optical fiber carrier 1024 may be moved to bypass obstructions 1030 as described above. In particular, the movement may move these elongate optical fiber carriers through, around, or between obstructions 1030.

In yet another illustrative example, ultrasound inspection system 1002 may emit light 1062 to cause sounds waves to travel in wing box 1008. Ultrasound inspection system 1004 may emit light 1061 to detect responses to the vibrations in wing box 1008 caused by ultrasound inspection system 1002 emitting light 1062.

With this implementation, number of optical fibers 1014 may be an example of first array of optical fibers 406 and number of optical fibers 1022 may be second array of optical fibers 408.

Figure 11:
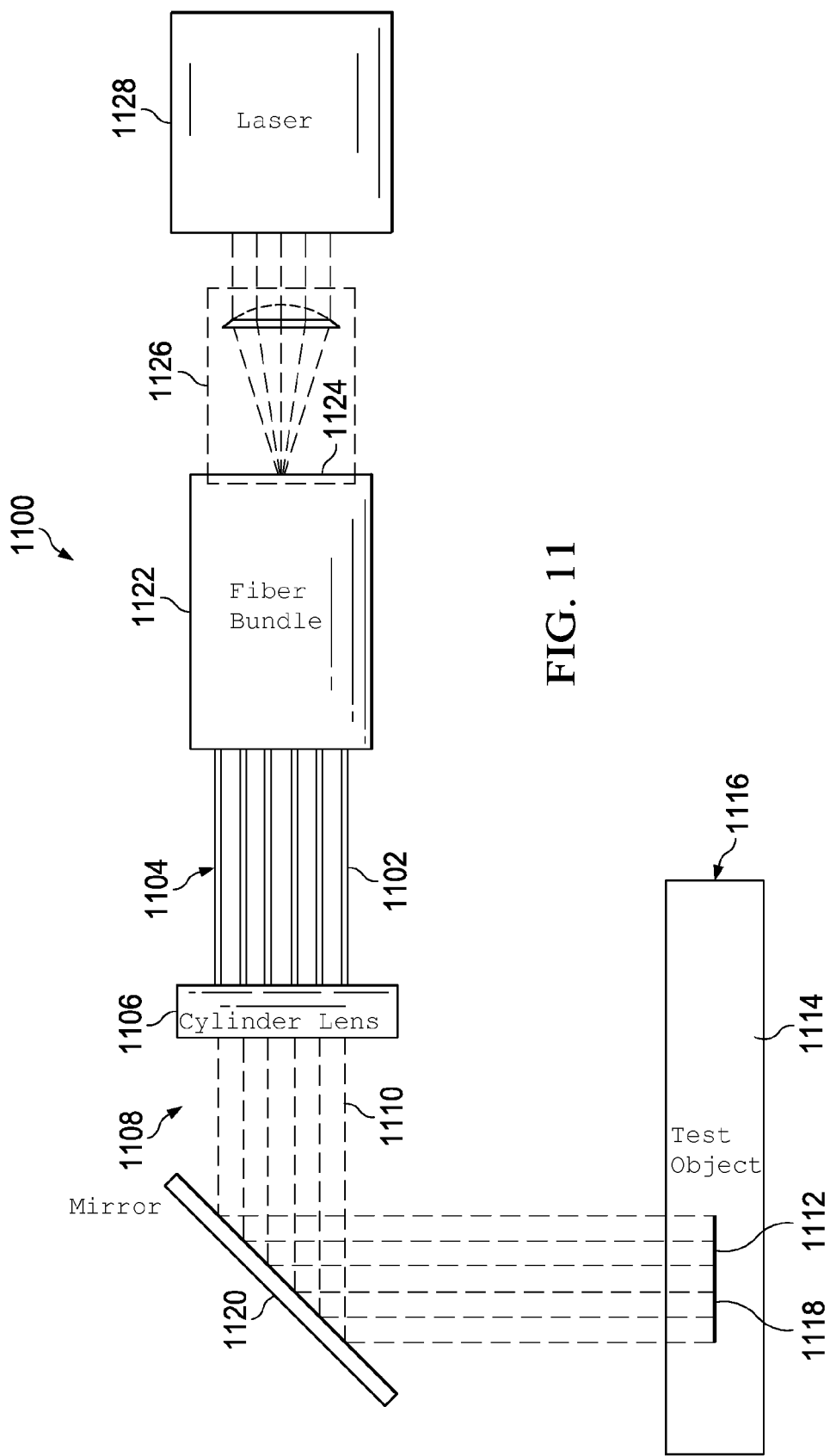
FIG. 11 is an illustration of an ultrasound source in accordance with an illustrative embodiment.

Turning now to FIG. 11, an illustration of an ultrasound source is depicted in accordance with an illustrative embodiment. Ultrasound source 1100 is an example of one implementation for ultrasound source 402 shown in block form in FIG. 4.

In this illustrative example, optical fibers 1102 are arranged in array 1104. Optical fibers 1102 may be implemented using any type of optical fiber that is configured to carry light within the optical fibers.

In this illustrative example, six optical fibers are present in optical fibers 1102. Array 1104 is a 1×6 array in this illustrative example. Of course, other numbers of optical fibers and other types of arrays may be used. For example, optical fibers 1102 may include three fibers, fifteen fibers, twenty-seven fibers, or some other suitable number of fibers. Further, in some illustrative examples, the array may have two or more rows instead of a single row of optical fibers.

Ultrasound source 1100 also includes cylinder lens 1106. Cylinder lens 1106 is configured to cause light 1108 transmitted by array 1104 of optical fibers 1102 to form beams 1110 which has a linear shape. Cylinder lens 1106 is configured to shape light 1108. In particular, cylinder lens 1106 is configured to cause light 1108 to form pattern 1112 on surface 1114 of test object 1116 as a contiguous line. In this illustrative example, cylinder lens 1106 may function to cause pattern 1112 of light 1108 to have an intensity with a Gaussian profile. In this illustrative example, the Gaussian profile is in an X and Y direction relative to a plane on surface 1114 of test object 1116.

In these illustrative examples, if optical fibers 1102 in array 1104 are spaced far enough apart, then a pattern of individual areas is formed on surface 1114 of test object 1116. Each area is "approximately a Gaussian profile" in both X and Y directions. Cylinder lens 1106 causes the Gaussian profiles to be different in the X and Y directions.

In particular, cylinder lens 1106 is configured to reduce divergence in a manner such that beams 1110 are focused in one direction and form pattern 1112 when reaching surface 1114 of test object 1116. In these illustrative examples, pattern 1112 takes the form of line 1118. Line 1118 may be formed from the intersection or overlapping of beams 1110 on surface 1114 of test object 1116. Without cylinder lens 1106, the divergence of beams 1110 may be in two dimensions resulting in an oval or circular shape rather than a line.

In this example, mirror 1120 is an example of a component that may be used to implement optics system 410 in FIG. 4. Mirror 1120 is configured to manage the direction in which beams 1110 of light 1108 travel to reach surface 1114 of test object 1116.

As depicted, optical fibers 1102 may be grouped and covered to form fiber bundle 1122. In this illustrative example, end 1124 of fiber bundle 1122 is connected to collimator 1126.

Collimator 1126 is connected to laser 1128. Laser 1128 is the source of light 1108. As depicted, light 1108 is sent through collimator 1126. Collimator 1126 is configured to make light 1108 coherent in these illustrative examples.

Figure 12:
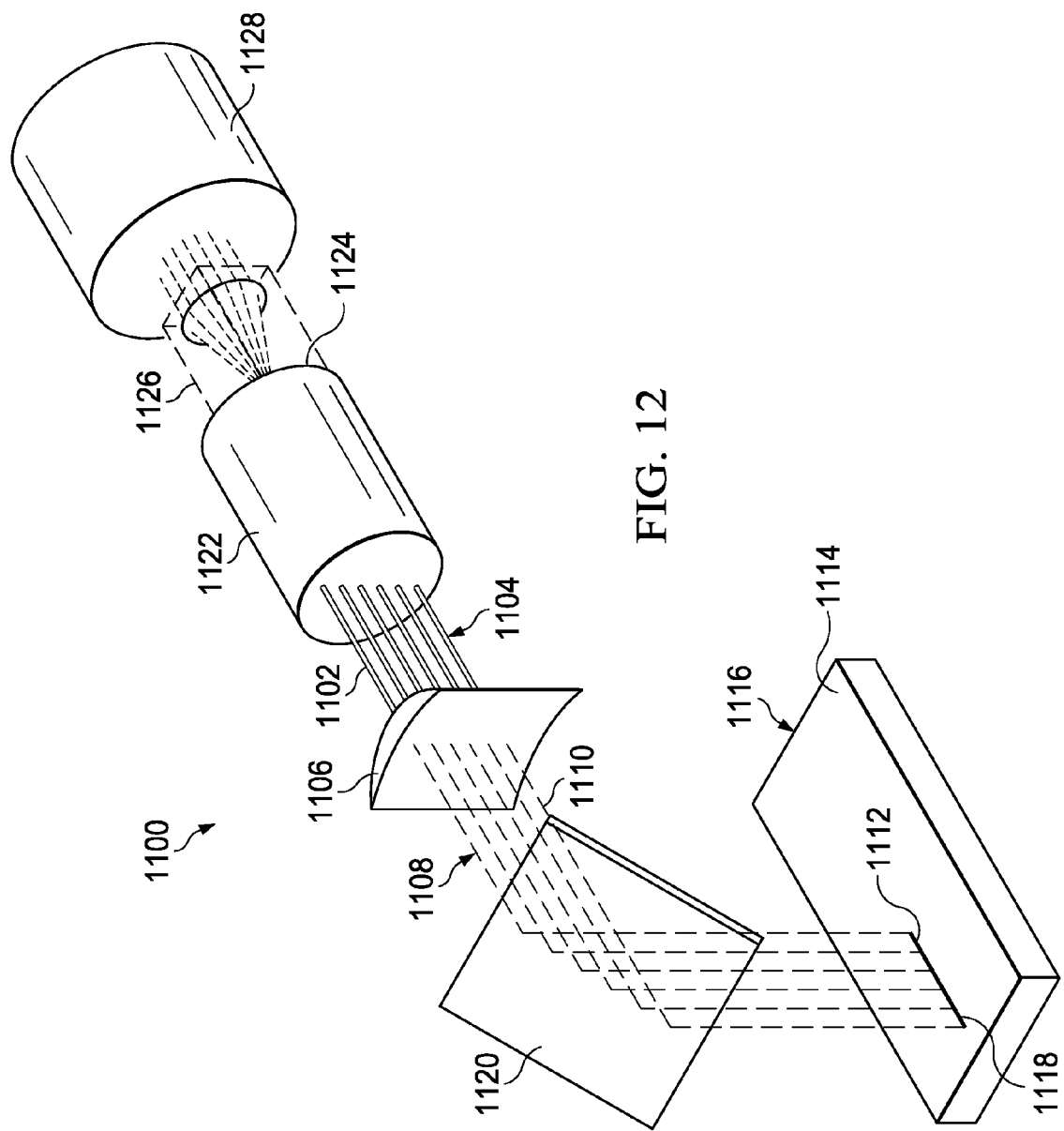
FIG. 12 is an illustration of an ultrasound source in accordance with an illustrative embodiment.

Turning now to FIG. 12, an illustration of an ultrasound source is depicted in accordance with an illustrative embodiment. In this depicted example, ultrasound source 1100 is shown in a perspective view.

Figure 13:
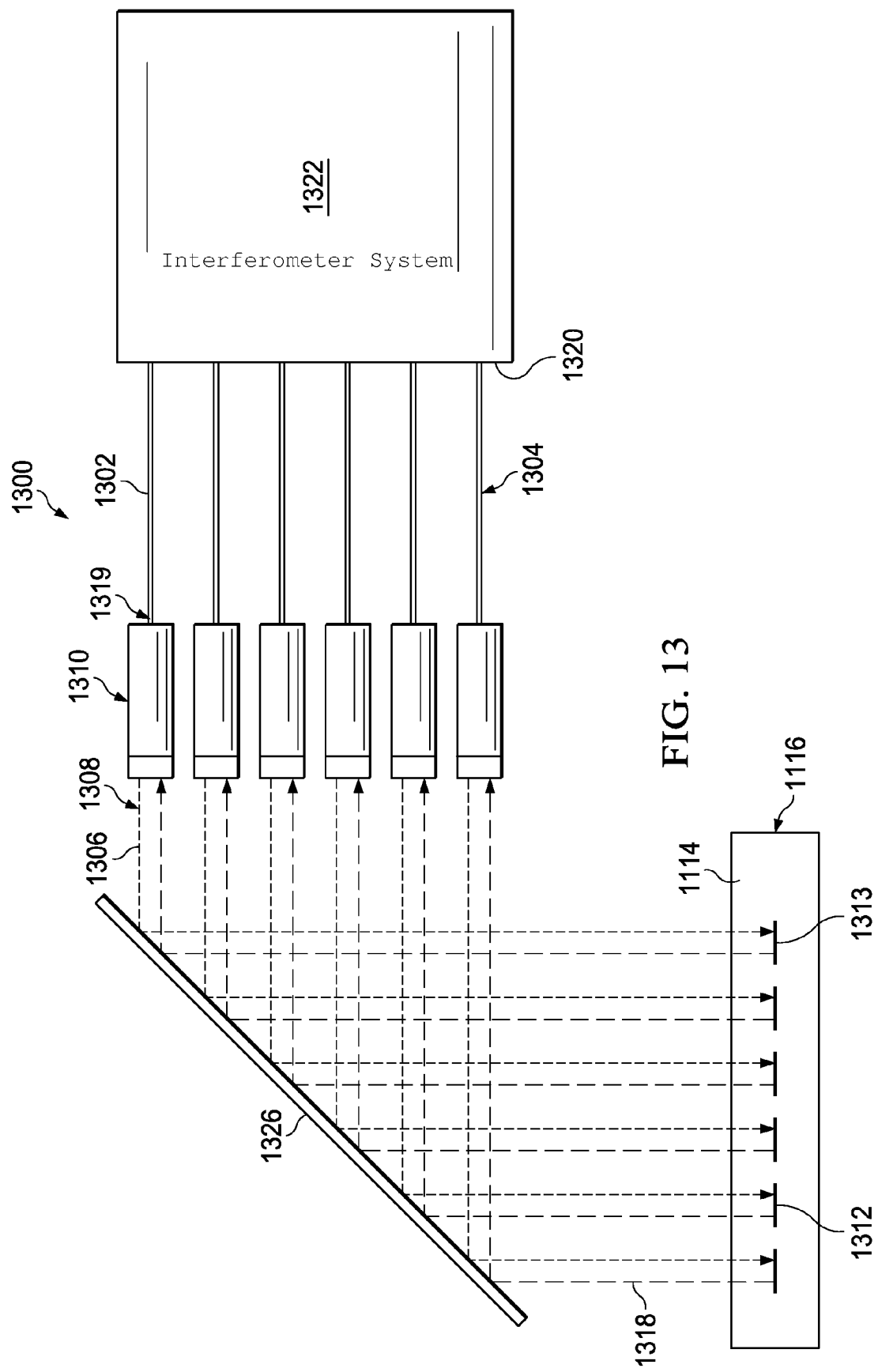
FIG. 13 is an illustration of an ultrasound detector in accordance with an illustrative embodiment.

Turning now to FIG. 13, an illustration of an ultrasound detector is depicted in accordance with an illustrative embodiment. Ultrasound detector 1300 is an example of one implementation for ultrasound detector 404 shown in block form in FIG. 4. As depicted, ultrasound detector 1300 includes optical fibers 1302. Optical fibers 1302 are arranged as array 1304. Array 1304 of optical fibers 1302 is configured to emit beams 1306 of light 1308.

In this illustrative example, six optical fibers are present in optical fibers 1302. Additionally, array 1304 is a 1×6 array. Of course, other numbers of optical fibers and other configurations for array 1304 may be present depending on the particular implementation.

In this illustrative example, ultrasound detector 1300 also includes collimators 1310. As depicted, each optical fiber in optical fibers 1302 is associated with a collimator in collimators 1310.

In these illustrative examples, collimators 1310 may be implemented using different types of collimators. For example, without limitation, collimators 1310 may be selected from at least one of an aspherical lens collimator, a spherical lens collimator, a grin lens collimator, or some other suitable type of collimator. Collimators 1310 are used to change light 1308 into coherent light in these illustrative examples.

Light 1308 is comprised of light waves that are in phase with each other. With light 1308, the phases of the electromagnetic waves at each point on a line normal to the direction of which the beams 1306 are traveling is identical.

In this illustrative example, beams 1306 of light 1308 form pattern 1312 on surface 1114 of test object 1116. In this illustrative example, pattern 1312 is in the form of line 1313. Line 1313 of pattern 1312 is a non-contiguous line in this illustrative example. In other illustrative examples, line 1313 of pattern 1312 may be a contiguous line.

In this illustrative example, light 1308 transmitted by optical fibers 1302 onto surface 1114 of test object 1116 results in response 1318. Response 1318 is comprised of light. The light in response 1318 is caused by interaction with surface 1114. For example, light 1308 may reflect, scatter, or reflect and scatter off of surface 1114.

Response 1318 is detected at end 1319 of optical fibers 1302 and may be transmitted through optical fibers 1302 in a direction opposite to the transmission of light 1308. In this illustrative example, end 1320 of optical fibers 1302 in array 1304 is connected to interferometer system 1322. Interferometer system 1322 is the source of light 1308 and receives response 1318.

In this illustrative example, mirror 1326 is an example of a component that may be used to implement optics system 410 in FIG. 4. Mirror 1326 is configured to control the direction in which light 1308 and response 1318 travel.

Figure 14:
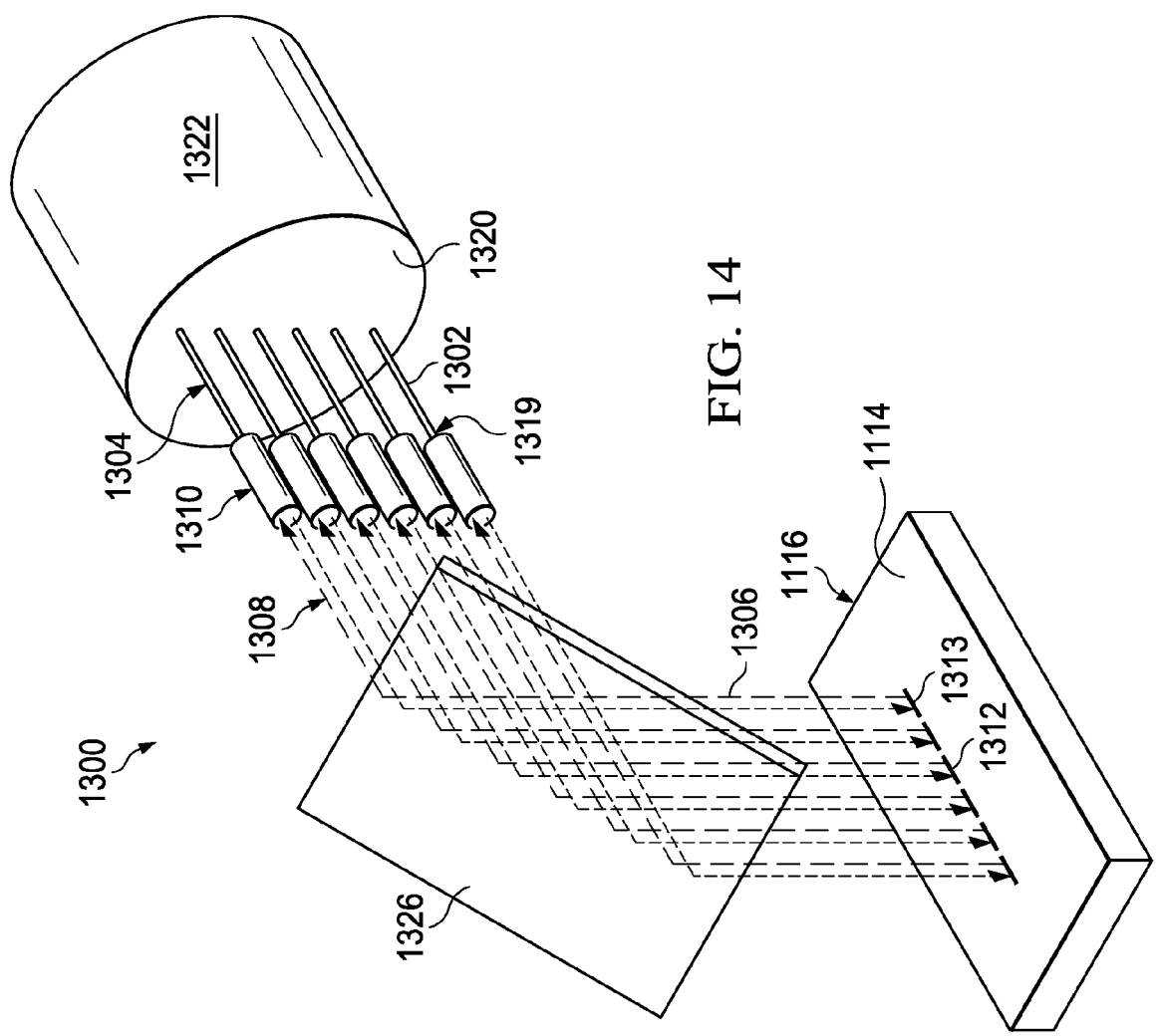
FIG. 14 is an illustration of an ultrasound detector in accordance with an illustrative embodiment.
Figure 15:
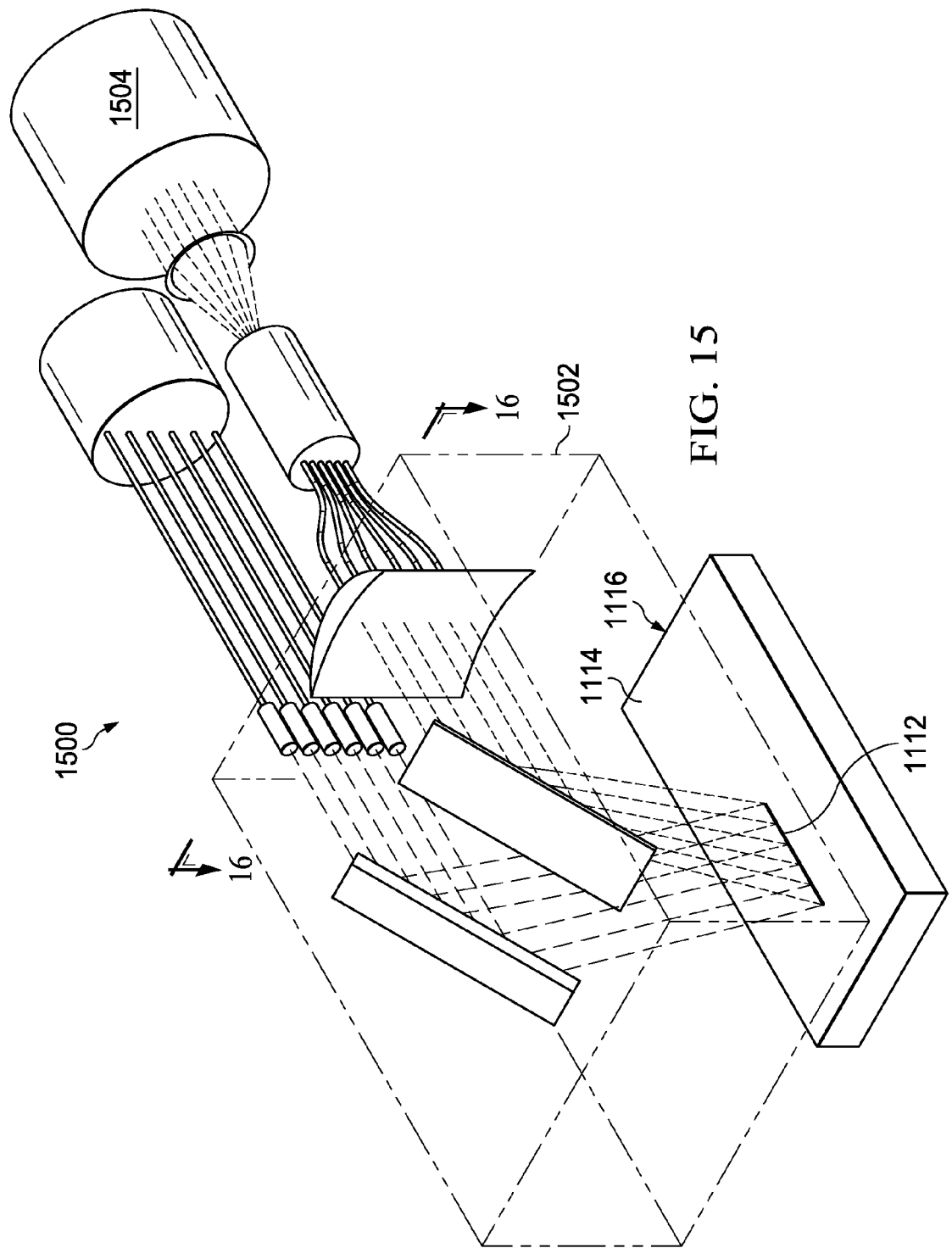
FIG. 15 is an illustration of an ultrasound inspection system in accordance with an illustrative embodiment.

Turning now to FIG. 14, an illustration of an ultrasound detector is depicted in accordance with an illustrative embodiment. In this illustrative example, a perspective view of ultrasound detector 1300 is shown. Turning now to FIG. 15, an illustration of an ultrasound inspection system is depicted in accordance with an illustrative embodiment. In this depicted example, a perspective view of ultrasound inspection system 1500 is shown. In this example, ultrasound inspection system 1500 includes ultrasound source 1100, ultrasound detector 1300, and sensor structure 1502. Sensor structure 1502 is an example of a sensor structure that may be located on an end of an elongate optical fiber carrier, such as on first end 604 of elongate optical fiber carrier 600 in FIG. 6, first end 704 on elongate optical fiber carrier 700 in FIG. 7, first end 804 on elongate optical fiber carrier 800 in FIG. 8, and first end 904 on elongate optical fiber carrier 900 in FIG. 9.

Sensor structure 1502 takes the form of a housing for an end effector in this illustrative example. As depicted, components for ultrasound source 1100 and ultrasound detector 1300 are located inside of sensor structure 1502 but not seen in this example.

Figure 16:
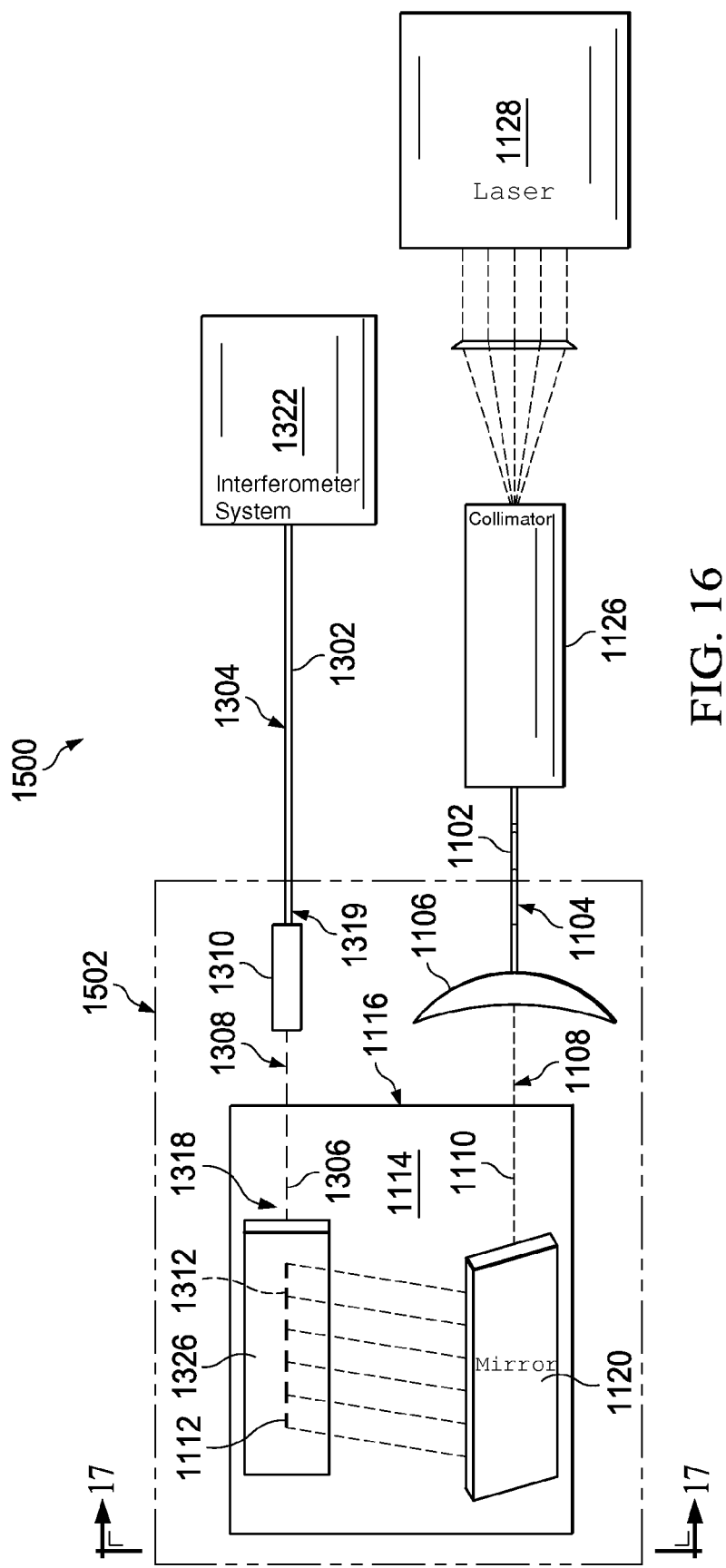
FIG. 16 is an illustration of a top view of an ultrasound inspection system in accordance with an illustrative embodiment.

Turning next to FIG. 16, an illustration of a top view of an ultrasound inspection system is depicted in accordance with an illustrative embodiment. In this view, sensor structure 1502 may be positioned over surface 1114 of test object 1116 to perform inspection of test object 1116.

In this illustrative example, pattern 1112 and pattern 1312 are aligned with each other on surface 1114 of test object 1116. In other words, pattern 1112 is transmitted onto the same location as pattern 1312 in this illustrative example. As a result, these two patterns substantially overlap each other.

Pattern 1112 of light 1108 is configured to generate sound waves within test object 1116. Responses to sound waves may cause vibrations in surface 1114 of test object 1116. Pattern 1312 of light 1308 is configured to generate response 1318 which includes variations or changes in surface 1114 due to vibrations caused by the response to the sound waves. Response 1318 is detected by optical fibers 1302.

In these illustrative examples, laser 1128 generates light 1108. Light 1108 is collimated by collimator 1126 in this illustrative example. This collimated light is then transmitted through optical fibers 1102 in the manner described with respect to FIG. 11 and FIG. 12.

In these illustrative examples, light 1308 may be generated by interferometer system 1322. Response 1318 to light 1308 may travel through optical fibers 1302 back to interferometer system 1322. Interferometer system 1322 may use response 1318 to generate data used to determine whether an inconsistency is present in test object 1116.

Figure 17:
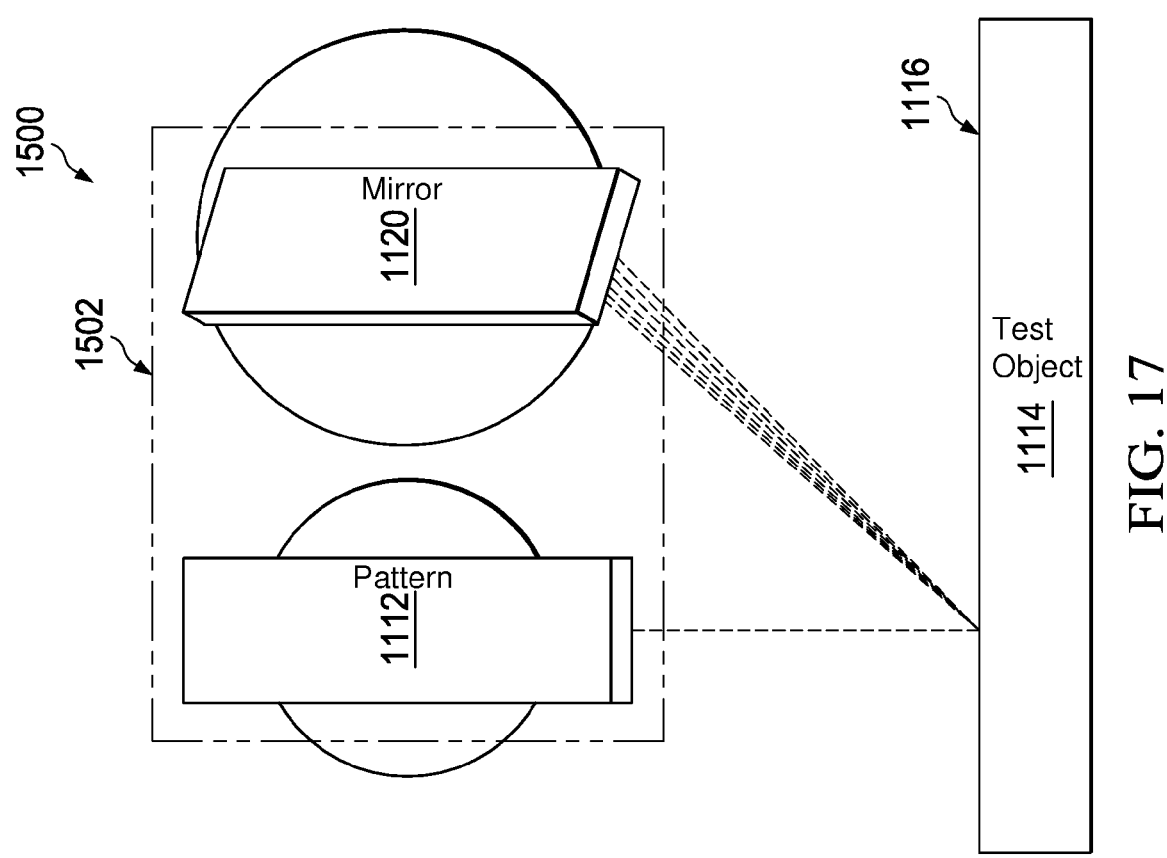
FIG. 17 is an illustration of a front view of an ultrasound inspection system in accordance with an illustrative embodiment.

Turning now to FIG. 17, an illustration of a front view of an ultrasound inspection system is depicted in accordance with an illustrative embodiment. In this illustrative example, another cross-sectional view of ultrasound inspection system 1500 is shown.

Figure 18:
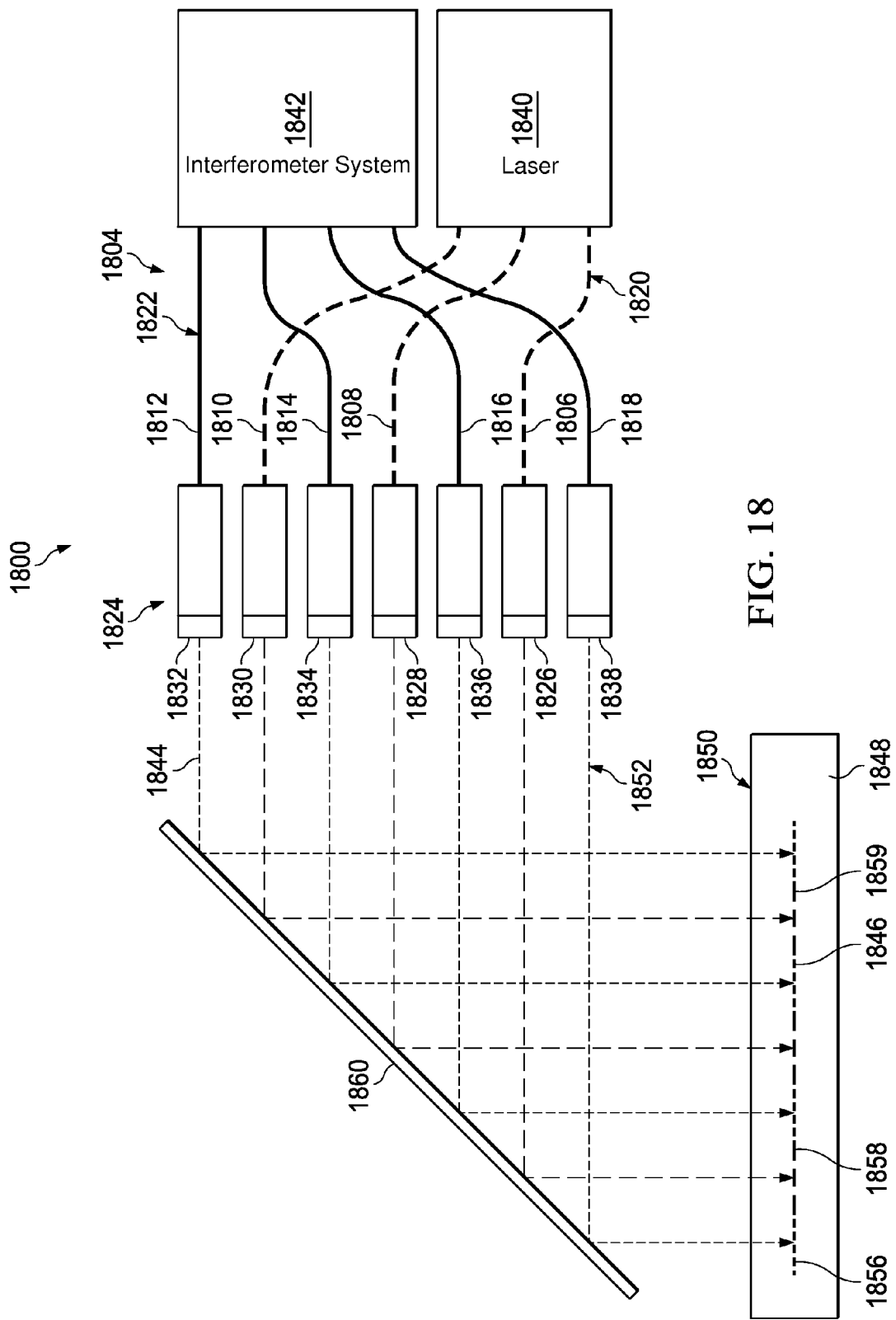
FIG. 18 is another illustration of an ultrasound inspection system in accordance with an illustrative embodiment.

Turning now to FIG. 18, another illustration of an ultrasound inspection system is depicted in accordance with an illustrative embodiment. As depicted, ultrasound inspection system 1800 is another example of an implementation for ultrasound inspection system 204 shown in block form in FIG. 2.

In this illustrative example, ultrasound inspection system 1800 includes optical fibers 1804. Optical fibers 1804 comprise optical fibers 1806, 1808, 1810, 1812, 1814, 1816, and 1818. Optical fibers 1806, 1808, and 1810 form first array of optical fibers 1820. Optical fibers 1812, 1814, 1816, and 1818 form second array of optical fibers 1822.

In this illustrative example, optical fibers 1804 are associated with collimators 1824. Collimators 1824 comprise collimators 1826, 1828, 1830, 1832, 1834, 1836, and 1838. Collimators 1826, 1828, and 1830 are associated with optical fibers 1806, 1808, and 1810, respectively. Collimators 1832, 1834, 1836, and 1838 are associated with optical fibers 1812, 1814, 1816, and 1818, respectively. In this illustrative example, optical fibers 1806, 1808, and 1810, in first array of optical fibers 1820, are interspersed with optical fibers 1812, 1814, 1816, and 1818 in second array of optical fibers 1822.

In this illustrative example, first array of optical fibers 1820 is connected to laser 1840. Second array of optical fibers 1822 is connected to interferometer system 1842. In this illustrative example, light 1844 from first array of optical fibers 1820 is emitted in the form of pattern 1846 onto surface 1848 of test object 1850. Light 1852 from second array of optical fibers 1822 forms pattern 1856 on surface 1848 of test object 1850.

In this illustrative example, pattern 1846 of light 1844 and pattern 1856 of light 1852 are non-contiguous lines. As depicted, pattern 1846 of light 1844 takes the form of line 1858, and pattern 1856 of light 1852 takes the form of line 1859. These two patterns of light encounter surface 1848 at substantially the same location. In other words, these two patterns of light would overlap each other if transmitted at the same time.

In this illustrative example, mirror 1860 is an example of an optical system that may be used to control the direction in which light 1844 and light 1852 travel. Mirror 1860 may be one implementation for optics system 410 shown in block form in FIG. 4.

Figure 19:
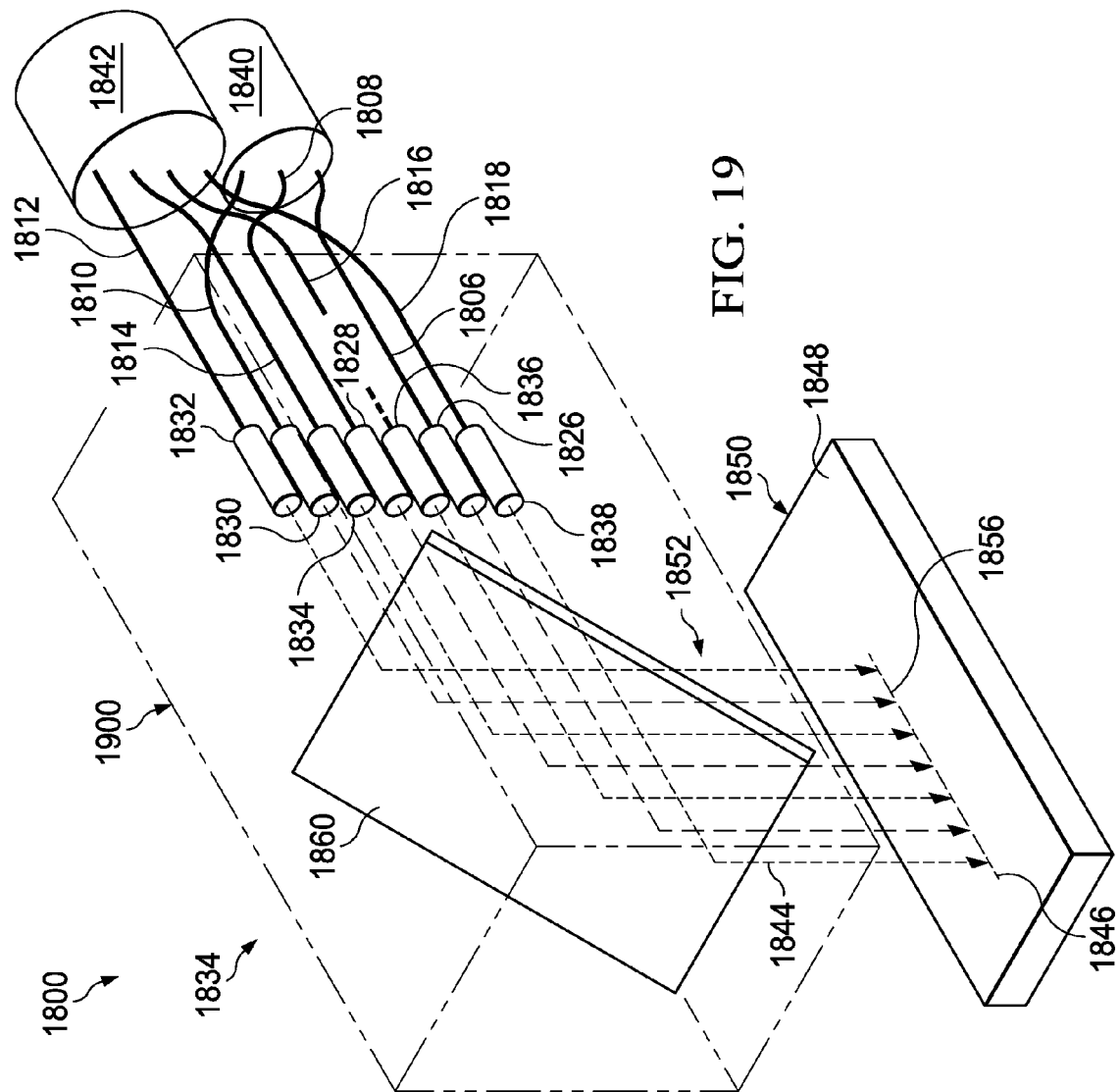
FIG. 19 is an illustration of a perspective view of an ultrasound inspection system in accordance with an illustrative embodiment.

Turning now to FIG. 19, an illustration of a perspective view of an ultrasound inspection system is depicted in accordance with an illustrative embodiment. In this perspective view, sensor structure 1900 is shown in phantom with some of the components in ultrasound inspection system 1800 being located within sensor structure 1900.

The illustration of the different embodiments of an ultrasound inspection system in FIGS. 11-19 is not meant to imply limitations in the way in which other illustrative embodiments may be implemented. For example, other numbers of optical fibers may be used other than those depicted. In still other illustrative examples, the light source for the first array of optical fibers and the second array of optical fibers may be a single light source.

In yet another illustrative example, a diffractive diffuser may be used to shape light 1108 emitted from array 1104 of optical fibers 1102. The diffractive diffuser may be used in addition to or in place of cylinder lens 1106.

The different components shown in FIG. 1 and FIG. 6-13 may be combined with components in FIGS. 2-5, used with components in FIGS. 2-5, or a combination of the two. Additionally, some of the components in FIG. 1 and FIGS. 6-13 may be illustrative examples of how components shown in block form in FIGS. 2-5 can be implemented as physical structures.

Figure 20:
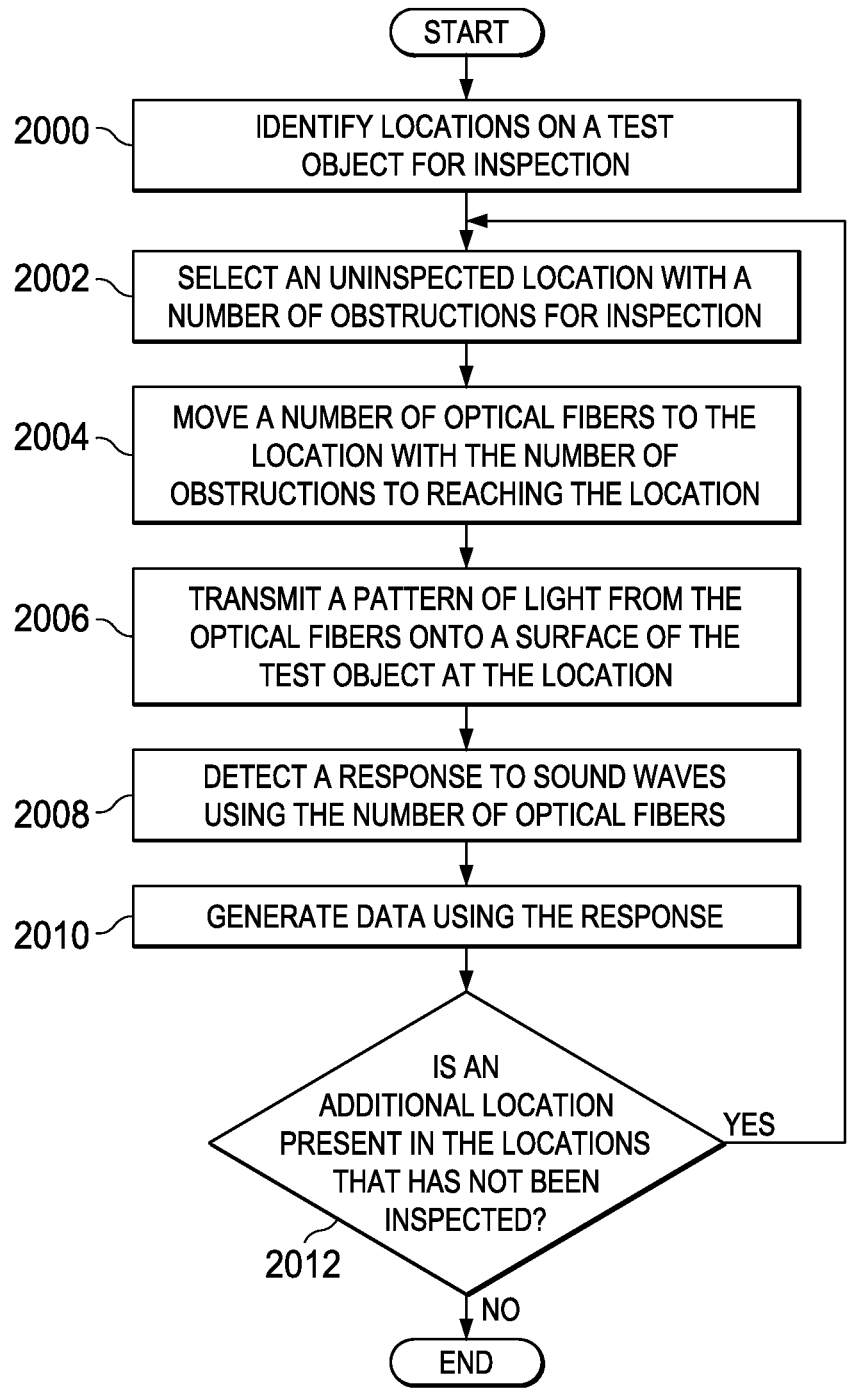
FIG. 20 is an illustration of a flowchart of a process for inspecting a location on a test object with a number of obstructions to reaching the location in accordance with an illustrative embodiment.

Turning now to FIG. 20, an illustration of a flowchart of a process for inspecting a location on a test object with a number of obstructions to reaching the location is depicted in accordance with an illustrative embodiment. The process illustrated in FIG. 20 may be implemented in inspection environment 200 in FIG. 2. In particular, the process may be implemented using ultrasound inspection system 204 to inspect test object 202.

The process begins by identifying locations on a test object for inspection (operation 2000). Next, the process selects an uninspected location with a number of obstructions for inspection (operation 2002).

The process then moves a number of optical fibers to the location with the number of obstructions to reaching the location (operation 2004). In these illustrative examples, the number of optical fibers may be moved to the location using an elongate optical fiber carrier. This elongate optical fiber carrier is configured to be moved in a manner that bypasses the obstructions to reaching the location where the inspection is desired. In this manner, the optical fibers held by the optical fiber carrier are moved to the location in operation 2004.

A pattern of light is transmitted from the optical fibers onto a surface of the test object at the location (operation 2006). The light is configured to cause sound waves in the test objects when the pattern of light encounters the surface of the test object.

A response to sound waves is detected using the number of optical fibers (operation 2008). In some illustrative examples, the optical fibers may be connected to, or part of, one or more interferometers. These devices may be used to detect the sound waves.

Next, data is generated using the response (operation 2010). This data may be used to determine whether an inconsistency is present at the location. The data may include information about the response as well as an identification of the information. This identification may be based on coordinates. The coordinates may use a coordinate system for the test object.

A determination is made as to whether an additional location is present in the locations that has not been inspected (operation 2012). If an additional location is present that has not been inspected, the process returns to operation 2002. Otherwise, the process terminates.

Figure 21:
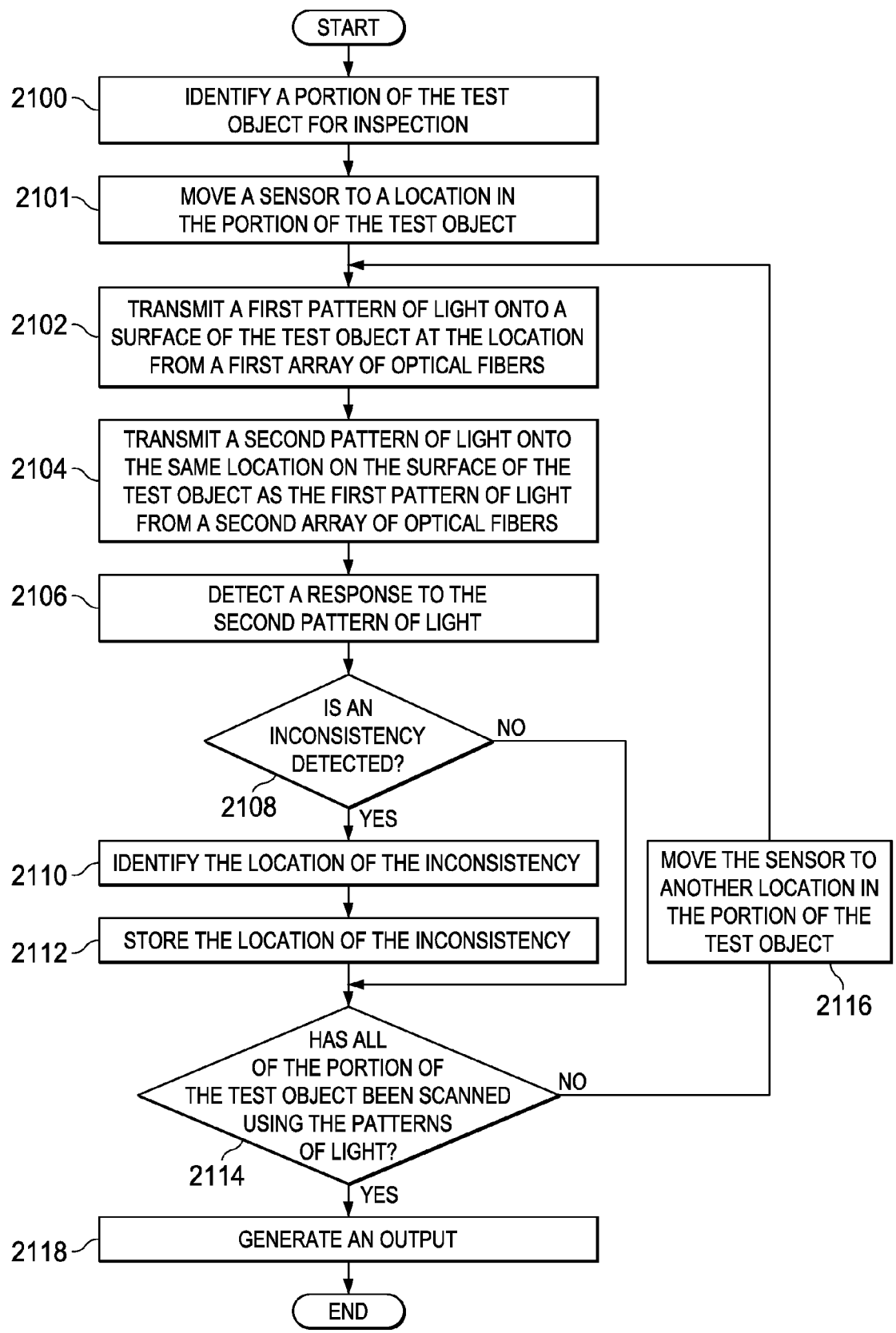
FIG. 21 is a flowchart of a process for scanning a test object in accordance with an illustrative embodiment.

Turning now to FIG. 21, a flowchart of a process for scanning a test object is depicted in accordance with an illustrative embodiment. In this illustrative example, the process in FIG. 21 may be implemented using ultrasound inspection system 204 in FIG. 2.

The process begins by identifying the portion of the test object for inspection (operation 2100). This portion of the test object may be some or the entire surface of the test object. For example, the portion of the test object may be a side, an edge, a radius, or some other portion of the test object.

A sensor is then moved to a location in the portion of the test object (operation 2101). In operation 2101, an orientation of the sensor may be adjusted to take into account a non-planar feature on the test object.

For example, the sensor may be positioned such that the pattern of light encompasses a non-planar feature not easily scanned by currently available laser ultrasound inspection systems. The non-planar feature may be, for example, a radius. The sensor may be moved in a linear direction along the length the radius.

In another illustrative example, the sensor may be positioned such that the pattern of light encompasses the margin of a part close to an edge where ultrasound coupling is difficult to achieve using currently available laser ultrasound inspection systems.

The process transmits a first pattern of light onto a surface of the test object at the location from a first array of optical fibers (operation 2102). In this illustrative example, the ray of light is transmitted in pulses and in a manner configured to cause sound waves in the test object. The location is a location in the portion of the test object that is to be inspected.

The process transmits a second pattern of light onto the same location on the surface of the test object as the first pattern of light from a second array of optical fibers (operation 2104). A response to the second pattern of light is detected (operation 2106). The response to the second pattern of light may be analyzed to identify a response to the sound waves that reach the surface of the test object.

A determination is made as to whether an inconsistency is detected (operation 2108). If an inconsistency is detected, the location of the inconsistency is identified (operation 2110). This location may be identified based on the response to sound waves detected using the response to the second pattern of light. The location of the inconsistency is stored (operation 2112).

A determination is made as to whether all of the portion of the test object has been scanned using the patterns of light (operation 2114). If all of the test object has not been scanned, the process moves the sensor to another location in the portion of the test object (operation 2116), with the process then returning to operation 2102 as described above.

If all of the portion of the test object has been scanned in operation 2114, an output is generated (operation 2118) with the process terminating thereafter. In operation 2118, the output may depend on whether one or more inconsistencies has been identified in the test object. If an inconsistency has been identified, at least one of an alert, an image with one or more graphical images identifying inconsistencies, a report, and other suitable types of output may be generated. Turning back to operation 2108, if an inconsistency is not detected, the process proceeds to operation 2114 as described above.

The different operations performed in FIG. 20 and FIG. 21 may be applied to test objects with planar and non-planar surfaces. These different operations may be performed for test objects that have non-planar features such as a radius, an edge, a groove, a ramp, a ply drop, a filler noodle, and other non-planar features.

Additionally, the different operations in FIG. 20 and FIG. 21 may be performed to inspect test objects more quickly than currently available laser ultrasound inspection systems that use a laser beam in the form of a point. Further, these operations may be performed without contact to the surface of a test object in contrast to laser ultrasound inspection systems that use piezoelectric transducers.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Illustrative embodiments of the present disclosure may be described in the context of aircraft manufacturing and service method 2200 as shown in FIG. 22 and aircraft 2300 as shown in FIG. 23. Turning first to FIG. 22, an illustration of an aircraft manufacturing and service method is depicted in accordance with an illustrative embodiment. During pre-production, aircraft manufacturing and service method 2200 may include specification and design 2202 of aircraft 2300 in FIG. 23 and material procurement 2204.

During production, component and subassembly manufacturing 2206 and system integration 2208 of aircraft 2300 in FIG. 23 takes place. Thereafter, aircraft 2300 in FIG. 23 may go through certification and delivery 2210 in order to be placed in service 2212. While in service 2212 by a customer, aircraft 2300 in FIG. 23 is scheduled for routine maintenance and service 2214, which may include modification, reconfiguration, refurbishment, and other maintenance or service.

Each of the processes of aircraft manufacturing and service method 2200 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 23, an illustration of an aircraft is depicted in which an illustrative embodiment may be implemented. In this example, aircraft 2300 is produced by aircraft manufacturing and service method 2200 in FIG. 22 and may include airframe 2302 with plurality of systems 2304 and interior 2306. Examples of systems 2304 include one or more of propulsion system 2308, electrical system 2310, hydraulic system 2312, and environmental system 2314. Any number of other systems may be included. Although an aerospace example is shown, different illustrative embodiments may be applied to other industries, such as the automotive industry.

Apparatus and methods embodied herein may be employed during at least one of the stages of aircraft manufacturing and service method 2200 in FIG. 22.

One or more illustrative embodiments may be used during component and subassembly manufacturing 2206. For example, ultrasound inspection system 204 in FIG. 2 may be used to test different components generated during component and subassembly manufacturing 2206. In particular, ultrasound inspection system 204 may be used to test composite objects that form different parts for aircraft 2300. Further, ultrasound inspection system 204 also may be used to perform inspections during maintenance and service 2214. For example, aircraft 2300 may be inspected during scheduled maintenance for aircraft 2300. Further, ultrasound inspection system 204 also may be used to inspect composite parts used during maintenance and service 2214.

Thus, one or more illustrative embodiments may be used to perform inspections of test objects. In particular, inspections may be performed on test objects that may have obstructions to reaching locations at which inspections are desired. The illustrative embodiments use a light-based ultrasound inspection system in which optical fibers may be carried on an elongate optical fiber carrier. The elongate optical fiber carrier is configured to move in a manner that bypasses the obstructions. In other words, the elongate optical fiber carrier may be deformed or changed in shape to move around or through obstructions.

With an ultrasound inspection system in accordance with an illustrative embodiment, inspections of test objects may be made with less expense and time. In some illustrative embodiments, disassembly of structures in the test object may be reduced or avoided to perform desired inspections of different locations that may have obstructions to reaching those locations.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   a platform;
   an interferometer system connected to the platform;
   an elongate optical fiber carrier connected to and extending from the interferometer system;
   a light source in optical communication with the elongate optical fiber carrier, the light source configured to emit a light;
   a movement system connected to the elongate optical fiber carrier, the movement system configured to move the elongate optical fiber carrier into an opening of a test object, to move into a cavity of the test object, and to bypass a number of obstructions while moving the elongate optical fiber carrier to a location that is inside the test object and obstructed from the opening by the number of obstructions while the interferometer system remains outside the opening;
   a fiber bundle inside the elongate optical fiber carrier, the fiber bundle comprising a first plurality of optical fibers, the fiber bundle configured to receive and then transmit the light from the light source;
   an end effector disposed on an end of the elongate optical fiber carrier, the end opposite the interferometer system, the end effector comprising:
      a cylinder lens inside the housing and in optical communication with the first plurality of optical fibers, wherein the cylinder lens is configured to cause the light to have a first Gaussian profile in an "X" direction relative to a plane and a second Gaussian profile in a "Y" direction relative to the plane, and wherein the cylinder lens is configured to cause the first Gaussian profile and the second Gaussian profile to be different;
      a first mirror inside the housing and in optical communication with the cylinder lens, the first mirror further disposed such that light emitted from the cylinder lens is transmitted in a pattern of light onto a test object, wherein the pattern of light is configured to cause sound waves in the test object and a response light from the test object;
      a second mirror inside the housing and configured to receive the response light; and
      a plurality of collimators configured to receive the response light from the second mirror;
   a second plurality of optical fibers inside the elongate optical fiber carrier, the second plurality of optical fibers connected to the plurality of collimators, each optical fiber of the second plurality of optical fibers connected to a corresponding collimator of the plurality of collimators; and
   wherein the interferometer system is configured to receive the response light and generate data from the response light, the data used to determine whether an inconsistency is present in the test object at the location.

2. The apparatus of claim 1, wherein the platform comprises a robotic arm.

3. The apparatus of claim 1, wherein the elongate optical fiber carrier comprises a hand-held tool.

4. The apparatus of claim 1, wherein the movement system comprises a plurality of joints.

5. The apparatus of claim 1, wherein the light source comprises a plurality of lasers, the apparatus further comprising:
   a delay line and a delay circuit separating the plurality of lasers, the delay line and the delay circuit configured to reduce cross-talk in optical fibers in the optical fiber carrier.

6. The apparatus of claim 1, further comprising:
   a number of optical elements configured to modify transmission of the light.

7. The apparatus of claim 6, wherein the number of optical elements is selected from the group consisting of: a lens, a mirror, a diffractive optical element, a polarizer, a wave plate, and a periodically poled Lithium niobate crystal.

8. A method of identifying an inconsistency using a platform, an interferometer system connected to the platform, an elongate optical fiber carrier connected to and extending from the interferometer system, a fiber bundle inside the elongate optical fiber carrier, the fiber bundle comprising a first plurality of optical fibers, the fiber bundle configured to receive and then transmit the light from the light source, an end effector disposed on an end of the elongate optical fiber carrier, the end opposite the interferometer system, a light source in optical communication with the elongate optical fiber carrier, the light source configured to emit a light, and a movement system connected to the elongate optical fiber carrier, the method comprising:
   moving, using the movement system, the elongate optical fiber carrier into a cavity of a test object through an opening of in the test object;
   bypassing a number of obstructions within the cavity while moving the elongate optical fiber carrier to a location that is inside the test object and obstructed from the opening by the number of obstructions while the interferometer system remains outside the opening;
   causing, using a cylinder lens inside the housing and in optical communication with the first plurality of optical fibers, the light to have a first Gaussian profile in an "X" direction relative to a plane and a second Gaussian profile in a "Y" direction relative to the plane;
   causing, using the cylinder lens, the first Gaussian profile and the second Gaussian profile to be different;
   transmitting, using a first mirror inside the housing and in optical communication with the cylinder lens, light emitted from the cylinder lens in a pattern onto a test object, wherein the pattern is configured to cause sound waves in the test object and a response light from the test object;
   receiving, at a second mirror inside the housing, the response light;
   receiving, at a plurality of collimators, the response light from the second mirror, wherein a second plurality of optical fibers is inside the elongate optical fiber carrier, the second plurality of optical fibers connected to the plurality of collimators, each optical fiber of the second plurality of optical fibers connected to a corresponding collimator of the plurality of collimators;
   receiving, at the interferometer system, the response light;
   generating data from the response light; and
   determining, using the data, whether an inconsistency is present in the test object at the location.

9. The method of claim 8, wherein the platform comprises a robotic arm.

10. The method of claim 8, wherein the elongate optical fiber carrier comprises a hand-held tool.

11. The method of claim 8, wherein the movement system comprises a plurality of joints and the method further comprises:
    bending the joints.

12. The method of claim 8, wherein the light source comprises a plurality of lasers, the method further comprising:
    reducing cross-talk in optical fibers in the optical fiber carrier using a delay line and a delay circuit separating the plurality of lasers.

13. The method of claim 8 further comprising:
modifying transmission of the light using a number of optical elements.

14. The method of claim 13, wherein the number of optical elements is selected from the group consisting of: a lens, a mirror, a diffractive optical element, a polarizer, a wave plate, and a periodically poled Lithium niobate crystal.

* * * * *